(12) United States Patent
Lin et al.

(10) Patent No.: US 6,800,618 B2
(45) Date of Patent: Oct. 5, 2004

(54) CHEMOSENSITIZING AGENTS AGAINST CHLOROQUINE RESISTANT PLASMODIUM FALCIPARUM AND METHODS OF MAKING AND USING THEREOF

(75) Inventors: Ai J. Lin, Gaithersburg, MD (US); Jian Guan, Silver Spring, MD (US); Dennis E. Kyle, Gaithersburg, MD (US); Wilbur K. Milhous, Germantown, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/849,400

(22) Filed: May 7, 2001

(65) Prior Publication Data

US 2003/0032801 A1 Feb. 13, 2003

(51) Int. Cl.[7] .................. A61K 31/33; A61K 31/54; C07D 279/14; C07D 513/00; C07D 417/00
(52) U.S. Cl. .................. 514/183; 514/299; 514/225.2; 514/225; 514/226; 544/14; 544/35; 544/41; 544/44; 548/566; 548/579; 546/152; 546/159
(58) Field of Search .................. 514/183, 299, 514/225.2, 225, 226, 224.8, 225.5, 225.8, 226.2, 411, 311, 313; 544/14, 35, 41, 44; 548/566, 579; 546/152, 159

(56) References Cited

U.S. PATENT DOCUMENTS

| 2,687,414 A | * | 8/1954 | Cusic | 544/41 |
|---|---|---|---|---|
| 5,599,815 A | | 2/1997 | Fukuda et al. | 514/254 |
| 5,741,791 A | * | 4/1998 | Olsen | 514/212 |

FOREIGN PATENT DOCUMENTS

| EP | 361485 | * | 4/1990 |
| HU | 66860 | * | 1/1995 |

OTHER PUBLICATIONS

Chemical Abstract DN 50: 1092 also cited as U.S.P. 2687414.*
Ford J.M. et al, "Pharmacology fo Drugs that Alter Multi-drug Resistance in Cancer", The Am.Soc. for Pharm & Exttl. There.42, 155–199(1990).*

(List continued on next page.)

*Primary Examiner*—Richard L. Raymond
*Assistant Examiner*—Sudhaker B. Patel
(74) *Attorney, Agent, or Firm*—Elizabeth Arwine

(57) ABSTRACT

A compound having the structural formula

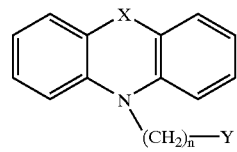

or a pharmaceutically acceptable salt or prodrug thereof, wherein X is a substituted or unsubstituted alkyl or a heteroatom; n is 4, 5 or 6; Y is a substituted or unsubstituted alkyl, cycloalkyl, heterocycloalkyl, aryl, heteroaryl, or

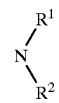

wherein $R_1$ and $R_2$ are each independently, H, a heteroatom, substituted or unsubstituted alkyl, cycloalkyl, heterocycloalkyl, aryl, or heteroaryl; and wherein each ring structure are independently substituted or unsubstituted is disclosed. Also disclosed are chemosensitizing agents and methods of modulating, attenuating, reversing, or affecting a cell's or organism's resistance to a given drug such as an antimalarial.

8 Claims, 3 Drawing Sheets

OTHER PUBLICATIONS

Pajeva et al;"Chem. Abstr. 128:289904, Molecular . . . phenothiazines as MDR" J.Med.Chem. 41/11. 1815–2623(1998).*

Wongsrichanalai et al, "Epidermalogy of drug–resist. Malaria";PuBMed. 11937421;Lancel Infect Dis Apr. 2/4, 209–18(2002).*

Rahman et al, "A randomised controlled treial on efficacy . . . Natl Malarial Cont. Prog.", PubMed: 11816441:Trans R. Soc. Trop.Med. Hyg 95/6,661–7(2001).*

McGready et al, "Artemisinin antimalarials in pregnancy . . . ", PubMed Abstr. 11712093; Clin Infect Dis 33/12, 2009–16(2001).*

Yoshitani, H., Japan Circulation J.,27/6, 487–98(1963), also cited ad Chemical Abstract DN 60:12388.*

Mehta et al, Severe acute renal failure in malaria;PubMed: 11590286:J.Postgrad Med. 47/1,24–6(2001).*

William T. Bellany, "P–Glycoproteins and Multidrug Resistance", 1996, Annu. Rev. Pharmacol. Toxicol., 36:161–183.

Jeffrey D. Chulay et al., "Plasmodium Falciparum: Assessment of in Vitro Growth by [$^3$H] Hypoxanthine Incorporation", (1983), Experimental Parasitology, 55:138–146.

James M. Ford et al., "Cellular and Biochemical Characterization of Thioxanthenes for Reversal of Multidrug Resistance in Human and Murine Cell Lines", (1990), Cancer Research. 50:1748–1756.

Samuel K. Martin et al., "Reversal of Chloroquine Resistance in Plasmodium Falciparum by Verapamil", (1987), Science, 235:899–901.

Wilbur K. Milhous et al., "In Vitro Strategies for Circumventing Antimalarial Drug Resistance", (1989), Malaria and the Red Cell, 2:61–72.

A.M.J. Oduola et al., "Reversal of Mefloqine Resistance with Penfluridol in Isolates of Plasmodium Falciparum from South–West Nigeria", (1993), Transactions of the Royal Society of Tropical Medicine and Hygene, 87:81–83.

H.L. Pearce et al., "Essential Features of the P–Glycoprotein Pharmacophore as Defined by a Series of Reserpine Analogs that Modulate Multidrug Resistance", (1989), Proc. Natl. Acad. Sci. USA, 86:5128–5132.

John M. Zamora et al., "Physical–Chemical Properties Shared by Compounds that Modulate Multidrug Resistance in Human Leukemic Cells", (1988), Molecular Pharmacology, 33:454–462.

Desjardins et al., Antimicrobial Agents Chemother, vol. 16: pp. 710–718, (1979).

Elion et al., "Antagonists of Nucleic Acid Derivatives", J. Biol. Chem. vol. 208: pp. 477–488, (1954).

Kyle et al., "Reversal of Plasmodium Falciparum Resist Ance To Chloroquine In Panamanian Aotus Monkeys", Am. J. Trop. Med. Hyg. vol. 48(1): pp. 126–133, (1993).

Milhous et al., Antimicrobial Agents Chemother, vol. 27: pp. 525–530, (1985).

Nooter et al., "Multidrug Resistance (mdr) Genes in Human Cancer", Br. j. Cancer, vol. 63: pp. 663–669, (1991).

Oduola et al., "Plasmodium Falciparum: Cloning by Single–Erythrocyte Micromanipulation and Heterogeneity in Vitro", Experimental Parasitology, vol. 66: pp. 86–95, (1988).

Rossan et al., "Comparison of Plasmodium Falciparum Infections In Panamanian and Colombian Owl Monkeys", Am. J. Trop. Med. Hyg., vol. 34(6): pp. 1037–1047, (1985).

Schmidt et al., Antimicrob Agents Chemother, vol. 11: pp. 826–843, (1977).

Schmidt, "Plasmodium Falciparum and Plasmodium Vivax Infections In The Owl Monkey (Aotus Trivirgatus)", Am. J. Trop. Med. Hyg., vol. 27(4): pp. 703–717, (1978).

Ye, Z.G., et al., Selective Antimalarial Activity of Tetrandrine Against Chloroquine Resistant Plasmodium Falciparum, (1989) Biochem Biophys. Res. Comm. 159:242–248.

Nooter, et al. (1991) BR. J. Cancer 63:663–669.

Nosten, F., et al. Mefloquine–Resistant Falciparum Malaria On The Thai–Burmese Border, (1991) Lancet 337:1140–1143.

Oduola, et al., (1988) Exp. Parasitol. 66:86–95.

Oduola, A.M., et al., Reduced In–Vitro Susceptibility To Mefloquine In West African Isolates Of Plasmodium Falciparum, (1987) Lancet 2: 1304–1305.

Pajeva, et al., Molecular Modeling Of Phenothiazines And Related Drugs As Multidrug Resistance Modifiers: A Comparative Molecular Field Analysis Study, (1998) J. Med. Chem. 41:1815–1826.

Reid, R. E., et al, Drug Interaction With Calmodulin: The Binding Site, (1983) J. Theor. Biol. 105:63–76.

Rossan, R. N., et al. (1985) Am J. Trop. Med. Hyg. 34:1037–47.

Schmidt, L. H. (1978) Am. J. Trop. Med. Hyg. 27:703–17.

Bitonti, A.J., et al., Reversal Of Chloroquine Resitance In Malaria Parasite Plasmodium Falciparum By Desiparamine, (1988) Science 242:1301–1303.

Foote, S.J., The Mode Of Action And The Mechanism Of Resistance To Antimalarial Drugs, (1994) 56:157–171.

Ford, J.M., et al., Structural Features Determining Activity Of Phenothiazines And Related Drugs For Inhibition Of Cell Growth And Reversal of Multi Drug Resistance, (1988) Mol. Pharmacol. 35:105–115.

Ford, J.M., et al., Pharmacology Of Drugs That Alter Multidrug Resistance In Cancer, (1990) The American Society for Pharmacology and Experimental Thereputics, 155–199.

Gerena, L., et al., Fluxetine Hydrochloride Enhances In Vitro Susceptibility To Chloroquine In Resistant Plasmodium Falciparum, (1992) Antimicrobial Agents and Chemotherapy 36:2761–2765.

Glennon, R. et al., Synthesis and Evaluation of Novel Alkylpiperazines As Potential Dopamine Antagonist, (1981) 24:678–683.

Kaiser, C., et al., Analogs of Phenothiazines: 5 Synthesis and Neuropharmacological Activity of Some Piperidylidene Derivatives Of Thioxanthenes, Xanthenes Dibenzoxepins, And Acridans, (1974) 17:57–62.

Kyle, D.E., et al., Plasmodium Falciparum: Modulation By Calcium Antagonist of Resistance To Chloroqine, Desethylchloroquine, Quinine, And Quinidine In Vitro, (1990) In Vitro. Trans Royal Soc. Trop. Med. Hyg. 84:474–478.

Magid, R.M., et al., Improvements In The Hexachloroacetone/Triphenylphosphine Procedure For The Conversion Of Allylic Alcohols Into Chlorides, (1981) J. Org. Chem. 46:824–825.

* cited by examiner

CHEMOSENSITIZING AGENTS AGAINST CHLOROQUINE RESISTANT PLASMODIUM FALCIPARUM AND METHODS OF MAKING AND USING THEREOF

ACKNOWLEDGEMENT OF GOVERNMENT SUPPORT

This invention was made by employees of the United States Army. The government has rights in the invention.

BACKGROUND OF THE INVENTION

1. Field of the Invention

The present invention generally relates to multidrug resistance and chemosensitizing agents. Specifically, the present invention relates to chemosensitizing agents for treating multiple drug resistant strains of *Plasmodium falciparum*.

2. Description of the Related Art

Multiple drug resistance (MDR) occurs when target cells, such as cancer cells, bacteria and protozoa, become resistant during treatment to the drug being used and to other drugs that are different and structurally unrelated to the drug. See Nooter, et al. (1991) *Br. J. Cancer* 63:663–669. Compounds such as verapamil, diltiazem, cyclosporin and catharanthine are known to attenuate or reverse drug resistance in some cells. However, not all cells that develop MDR are responsive to known chemosensitizing agents and some chemosensitizing agents are only active in vivo at or near toxic levels. Additionally, antipsychotic, antihistaminic or cardiovascular side effects are associated with some chemosensitizing agents.

MDR is a prevalent problem in the treatment of many diseases and infections. For example, the increasing prevalence of MDR strains of *Plasmodium falciparum* in most malaria endemic areas has significantly reduced the efficacy of current antimalarial drugs for treating, preventing or inhibiting malaria. Resistance to the inexpensive antimalarial mainstays, such as chloroquine, is problematic worldwide. Unfortunately, resistance to mefloquine, which was proposed as the drug of choice for chloroquine-resistant malaria, has been reported from Africa and Southeast Asia. See Nosten, F., et al. (1982) *Lancet* 337:1140–1143; and Oduola, A. M., et al. (1987) *Lancet* 2:1304–1305.

A wide variety of drugs representing different drug classes and diverse chemical structures have been shown to reverse chloroquine resistance in *P. falciparum* in vitro. See Gerena, L., et al. (1992) *Antimicrobial Agents and Chemotherapy* 36:2761–2765; Bitonti, A. J., et al. (1988) *Science* 242:1301–1303; and Ye, Z. G., et al. (1989) *Biochem Biophys. Res. Comm.* 159:242–248. These include calcium channel blockers (verapamil) and calmodulin antagonists (trifluoperazine and phenothiazines), which could be co-administered with chloroquine to effectively potentiate its efficacy against chloroquine resistant cell lines. See Kyle, D. E., et al. (1990) *In Vitro. Trans. Royal Soc. Trop. Med. Hyg.* 84:474–478 and Ford, J. M., et al. (1989) *Mol. Pharmacol.* 35:105–115. However, the clinical value of these compounds as MDR reversing agents is impaired by their profound antipsychotic, antihistaminic or cardiovascular side effects. Additionally, the effective dose of these compounds as chemosensitizing agents is generally close to or higher than the therapeutic dose for other clinical applications.

Extensive structure-activity relationship studies of neoplastic MDR modulators with diverse chemical structures have established two pharmacophores for resistance reversal activity: a hydrophobic tricyclic aromatic ring and a specific side chain with two amino groups separated by two or three carbons from the aromatic ring. Tertiary substituted amines are more potent than secondary or primary amines. However, antipsychotic and antihistaminic agents also share similar structural features, except for the length of side chain, as those of chemosensitizing agents. See Magid, R. M., et al. (1981) *J. Org. Chem.* 46:824–825.

For example, phenothiazines with ring nitrogen and side chain nitrogen separated by two carbons showed the best antihistaminic activity and those separated by three carbons exhibited the strongest antipsychotic activity. Thus, the length of side chain affects the pharmacological properties of the molecule. While the optimal side chain length of phenothiazine and related compounds for antihistaminic and antipsychotic activities is limited to 2–3 carbons, the optimal side chain length for anti-MDR activity has yet to be discovered.

Therefore, a need exists for chemosensitizing agents with improved anti-MDR efficacy and reduced side effects to restore the clinical efficacy of current drugs such as antimalarial drugs.

SUMMARY OF THE INVENTION

The present invention relates to a compound having the structural formula

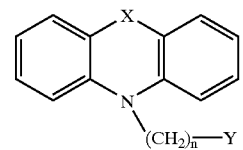

or a pharmaceutically acceptable salt or prodrug thereof, wherein X is a substituted or unsubstituted alkyl or a heteroatom; n is 4, 5 or 6; Y is a substituted or unsubstituted alkyl, cycloalkyl, heterocycloalkyl, aryl, heteroaryl, or

wherein $R_1$ and $R_2$ are each independently, H, a heteroatom, substituted or unsubstituted alkyl, cycloalkyl, heterocycloalkyl, aryl, or heteroaryl; and wherein each aromatic ring structure may be independently substituted or unsubstituted.

In some embodiments, X is C, S, or ethyl.

In some embodiments, Y is pyrrolidinyl, piperidinyl, morpholinyl, or 4-methylpiperazinyl.

In some embodiments, $R_1$ and $R_2$ are each independently, methyl, ethyl, or benzyl.

The compound of the present invention modulates, attenuates, reverses, or affects a cell's or organism's resistance to a given drug or compound such as an antimalarial.

Preferred compounds of the present invention include 10-(4-Dimethylaminobutyl)phenothiazine, 10-(4-Diethylaminobutyl)phenothiazine, 10-(4-Methylbenzylaminobutyl)phenothiazine, 10-(4-Dibenzylaminobutyl)phenothiazine, 10-(4-Pyrrolidin-1-yl-butyl)phenothiazine, 10-(4-Piperidin-1-yl-butyl)phenothiazine, 10-(4-Morpholin-4-yl-butyl)phenothiazine, 10-[4-(4-Methyl-piperazin-1-yl)-butyl]phenothiazine, 5-(4-Dimethylaminobutyl)iminodibenzyl, 5-(4-Diethylaminobutyl)iminodibenzyl, 5-(4-Methylbenzylaminobutyl)iminodibenzyl,
5-(4-Dibenzylaminobutyl)iminodibenzyl,
5-(4-Pyrrolidin-1-yl-butyl)iminodibenzyl,
5-(4-Piperidin-1-yl-butyl) iminodibenzyl,
5-(4-Morpholin-4-yl-butyl)iminodibenzyl,
5-[4-(4-Methyl-piperazin-1-yl)-butyl]iminodibenzyl,
5-(4-Diethylaminobutyl)iminostilbene,
5-(4-Pyrrolidin-1-yl-butyl)iminostilbene,
N,N-Diethyl-N',N'-diphenyl-butane-1,4-diamine,
Diphenyl-(4-pyrrolidin-1-yl-butyl)amine,
5-(5-Diethylaminopentyl)iminodibenzyl,
5-(5-Pyrrolidin-1-yl-pentyl)iminodibenzyl,
5-(6-Diethylaminohexyl)iminodibenzyl, and
5-(6-Pyrrolidin-1-yl-hexyl)iminodibenzyl.

In some embodiments, the present invention relates to a pharmaceutical composition comprising a compound having the structural formula

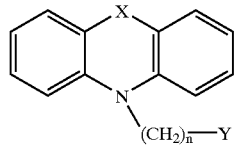

or a pharmaceutically acceptable salt or prodrug thereof, wherein X is a substituted or unsubstituted alkyl or a heteroatom; n is 4, 5 or 6; Y is a substituted or unsubstituted alkyl, cycloalkyl, heterocycloalkyl, aryl, heteroaryl, or

wherein $R_1$ and $R_2$ are each independently, H, a heteroatom, substituted or unsubstituted alkyl, cycloalkyl, heterocycloalkyl, aryl, or heteroaryl; wherein each aromatic ring structure may be independently substituted or unsubstituted; and a pharmaceutically acceptable excipient. The pharmaceutical composition may further comprise a supplementary active compound.

The present invention also relates to a chemosensitizing agent comprising a compound having the structural formula

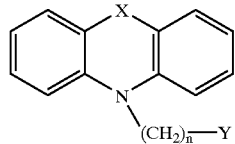

or a pharmaceutically acceptable salt or prodrug thereof, wherein X is a substituted or unsubstituted alkyl or a heteroatom; n is 4, 5 or 6; Y is a substituted or unsubstituted alkyl, cycloalkyl, heterocycloalkyl, aryl, heteroaryl, or

wherein $R_1$ and $R_2$ are each independently, H, a heteroatom, substituted or unsubstituted alkyl, cycloalkyl, heterocycloalkyl, aryl, or heteroaryl; and wherein each aromatic ring structure may be independently substituted or unsubstituted.

In some embodiments, the fractional inhibitory concentration of the chemosensitizing agent is less than 0.6, preferably less than about 0.5, preferably less than about 0.4, preferably less than about 0.3, more preferably about less than about 0.2. The compound of the chemosensitizing agent modulates, attenuates, reverses, or affects a cell's or organism's resistance to a given drug or compound such as an antimalarial.

In some embodiments, the present invention relates to a method of modulating, attenuating, reversing, affecting, or a combination thereof, a cell's or organism's resistance to a given drug comprising administering a compound having the structural formula

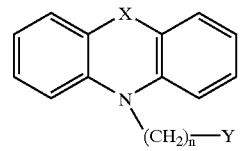

or a pharmaceutically acceptable salt or prodrug thereof, wherein X is a substituted or unsubstituted alkyl or a heteroatom; n is 4, 5 or 6; Y is a substituted or unsubstituted alkyl, cycloalkyl, heterocycloalkyl, aryl, heteroaryl, or

wherein $R_1$ and $R_2$ are each independently, H, a heteroatom, substituted or unsubstituted alkyl, cycloalkyl, heterocycloalkyl, aryl, or heteroaryl; and wherein each aromatic ring structure may be independently substituted or unsubstituted.

In some embodiments, the present invention relates to a method of treating, preventing, or inhibiting malaria in a subject comprising administering to the subject a therapeutically effective amount of a compound having the structural formula

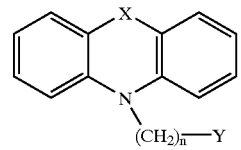

or a pharmaceutically acceptable salt or prodrug thereof, wherein X is a substituted or unsubstituted alkyl or a heteroatom; n is 4, 5 or 6; Y is a substituted or unsubstituted alkyl, cycloalkyl, heterocycloalkyl, aryl, heteroaryl, or

wherein $R_1$ and $R_2$ are each independently, H, a heteroatom, substituted or unsubstituted alkyl, cycloalkyl, heterocycloalkyl, aryl, or heteroaryl; and wherein each aromatic ring structure may be independently substituted or unsubstituted.

It is to be understood that both the foregoing general description and the following detailed description are exemplary and explanatory and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

This invention is further understood by reference to the drawings wherein.

DETAILED DESCRIPTION OF THE INVENTION

Figure 1:
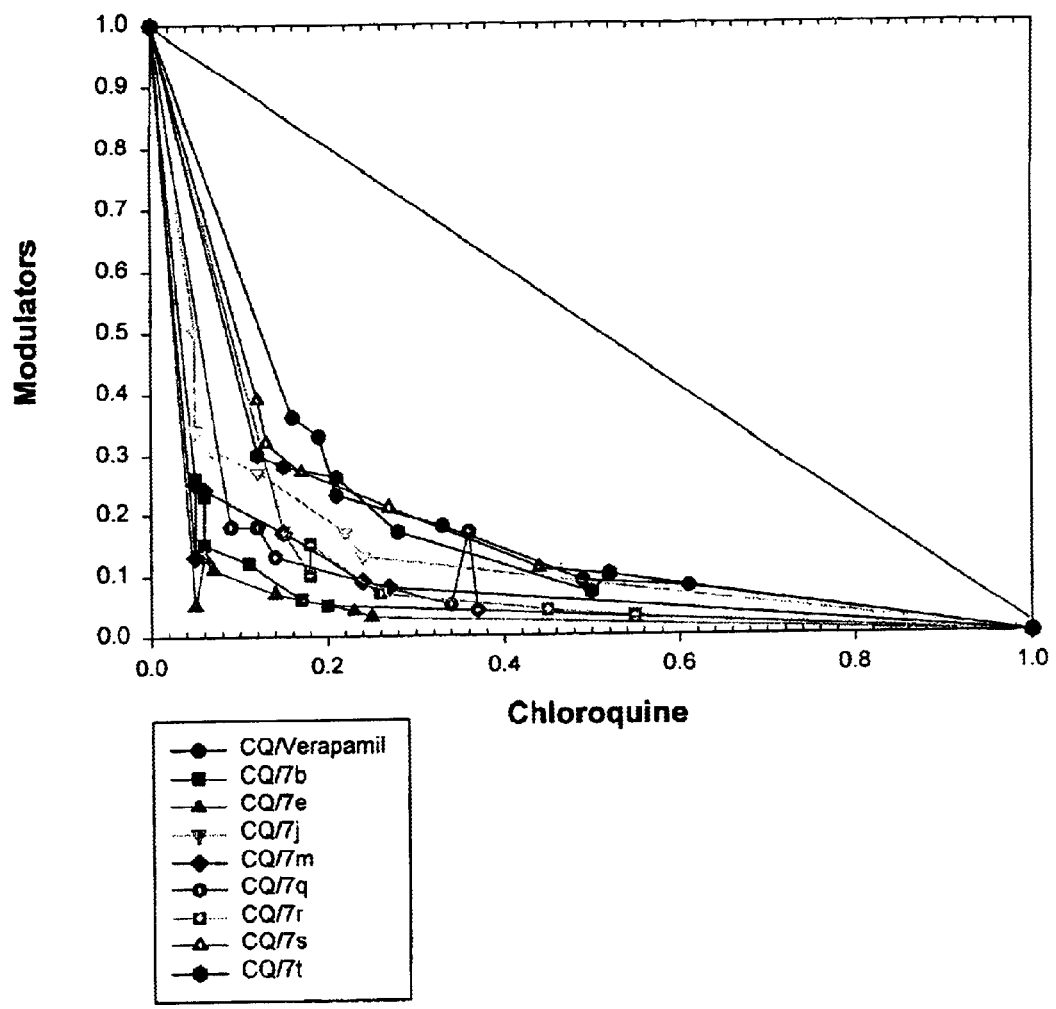
FIG. 1 is an isobologram of the interaction of chloroquine with modulators against W2 clone.

The present invention provides chemosensitizing agents with improved anti-MDR efficacy and reduced side effects to restore the clinical efficacy of current drugs such as antimalarials including mefloquine and chloroquine.

The chemosensitizing agents of the invention were designed and synthesized in an attempt to fabricate modulators with enhanced efficacy and minimal side effects against chloroquine resistant *Plasmodium falciparum*. In designing the chemosensitizing agents of the present invention, the structural features of prior art modulators against multi-drug resistant cancer cell lines such as multinucleus aromatic rings and disubstituted amino groups linked by an alkyl bridges were contemplated. Four aromatic amine ring systems, phenothiazine, iminodibenzyl, iminostilbene and diphenylamine were examined. Various tertiary amino groups including both noncyclic aliphatic and cyclic amines were introduced to explore steric tolerance at the end of the side chain.

Synergistic effects of the chemosensitizing agents of the present invention with mefloquine and chloroquine were observed in mefloquine resistant and chloroquine resistant *P. falciparum* clones in vitro. Specifically, the chemosensitizing agents of the present invention showed better resensitizing activity in chloroquine resistant than mefloquine resistant cell lines and were generally more effective against chloroquine resistant *P. falciparum* in Southeast Asian isolates, W2 and TM91C235, than in South America isolates, PC49 and RCS. Some of the analogs displayed moderate intrinsic in vitro antimalarial activity against W-2 clone of *P. falciparum*.

Elongation of the alkyl side chain retained the modulating activity, with four carbon bridge analogs being the most active. Compounds with phenothiazine rings exhibited the best chemosensitizing activity among the four different ring systems examined. Steric tolerance at terminal amino function is limited as evidenced by the dramatic loss of modulating activity when the size of substituents increased.

The chemosensitizing agent of the present invention exhibiting the most activity combines all three optimized structural features, which comprises a phenothiazine ring and a pyrrolidinyl group joined by a four-carbon alkyl bridge. The fractional inhibitory concentration (FIC) index of this chemosensitizing agent, compound 7e, is 0.21, which is superior to verapamil (0.51), which is one of the best known modulators in the prior art. The FIC is the actual $IC_{50}$ of one drug in the presence of the second drug but is expressed as a fraction of its $IC_{50}$ when used alone.

Thus, the present invention provides compounds of the general Structural Formula A as follows:

Structural Formula A

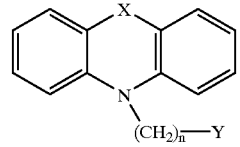

wherein X is a substituted or unsubstituted alkyl or a heteroatom;

n is 4, 5 or 6;

Y is a substituted or unsubstituted alkyl, cycloalkyl, heterocycloalkyl, aryl, heteroaryl, or

wherein $R_1$ and $R_2$ are each independently, H, a heteroatom, substituted or unsubstituted alkyl, cycloalkyl, heterocycloalkyl, aryl, or heteroaryl; and wherein the aromatic ring structures may be each independently further substituted.

In some embodiments of the invention, X is C, S or ethyl.

In some embodiments of the invention, Y is pyrrolidinyl, piperidinyl, morpholinyl, or 4-methylpiperazinyl.

In some embodiments of the invention, $R_1$ or $R_2$ are each independently, methyl, ethyl, or benzyl.

Several terms employed throughout the present application are described below.

As used herein, a "chemosensitizing agent" is an agent which modulates, attenuates, reverses, or affects a cell's or organism's resistance to a given drug or compound. The terms "modulator", "modulating agent", "attenuator", "attenuating agent", or "chemosensitizer" may be used alternatively to mean "chemosensitizing agent".

In accordance with a convention used in the art,

is used in structural formulas herein to depict the bond that is the point of attachment of the moiety or substituent to the core or backbone structure.

As used herein, the term "comprising" is used in the open sense, i.e., in the typical sense to denote inclusiveness.

Where chiral carbons are included in chemical structures, unless a particular orientation is depicted, both sterioisomeric forms are intended to be encompassed.

An "alkyl group" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (Bu), isobutyl (i-Bu), t-butyl (t-Bu), ethenyl, pentenyl, butenyl, propenyl, ethynyl, butynyl, propynyl, pentynyl, hexynyl, and the like, which may be unsubstituted (i.e., contain only carbon and hydrogen) or substituted by one or more suitable sustituents as defined below (e.g., one or more halogen, such as F, Cl, Br, or I, with F and Cl being preferred). A "lower alkyl group" is intended to mean an alkyl group having from 1 to 8 carbon atoms in its chain.

A "cycloalkyl group" is intended to mean a non-aromatic monovalent monocyclic, bicyclic, or tricyclic radical comprising 3–14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include the following moieties:

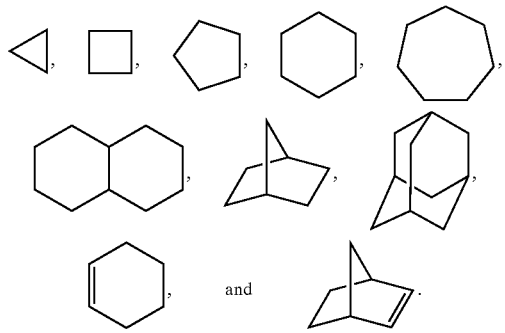

A "heterocycloalky group" is intended to mean a non-aromatic monovalent monocyclic, bicyclic, or tricyclic radical, which is saturated or unsaturated, comprising 3–18 ring members, which includes 1–5 heteroatoms selected from nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

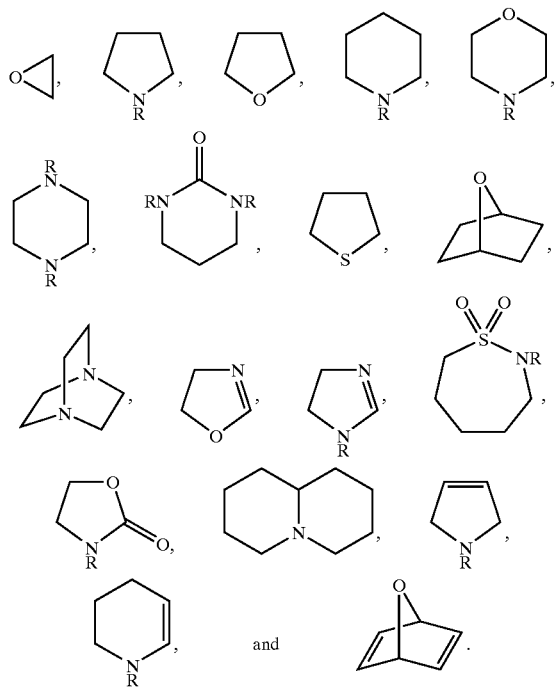

An "aryl group" is intended to mean an aromatic monovalent monocyclic, bicyclic, or tricyclic radical comprising 6, 10, 14, or 18 carbon ring members, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Illustrative examples of aryl groups include the following moieties:

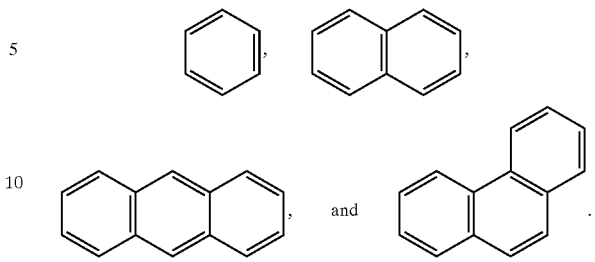

A "heteroaryl group" is intended to mean an aromatic monovalent monocyclic, bicyclic, or tricyclic radical comprising 4–18 ring members, including 1–5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

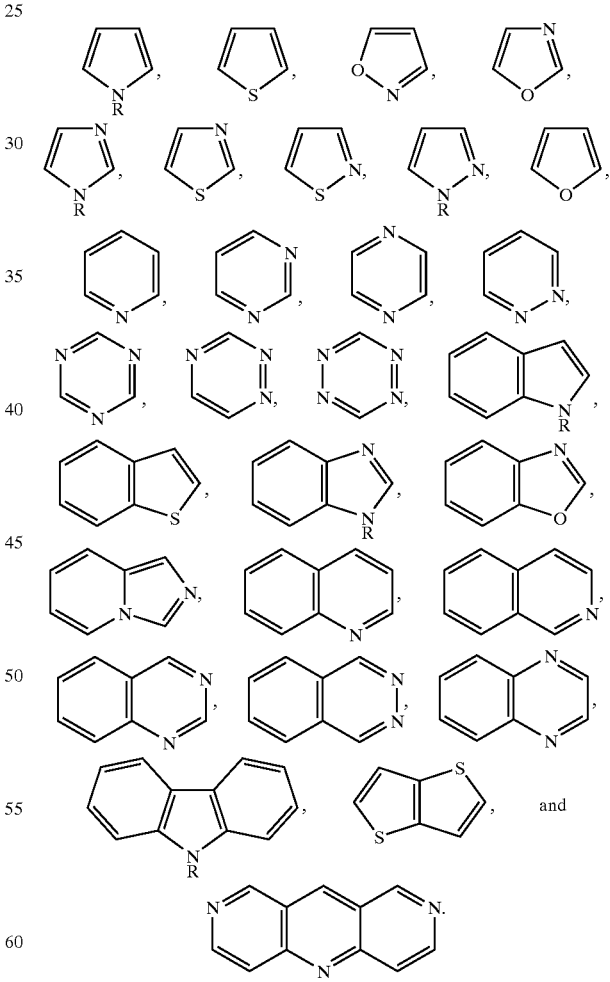

A "heterocycle" is intended to mean a heteroaryl or heterocycloalkyl group (each of which, as defined above, are optionally substituted).

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like.

An "acyl group" is intended to mean a —C(O)—$R_a$ radical, where $R_a$ is a suitable substituent as defined below.

A "thioacyl group" is intended to mean a —C(S)—$R_a$ radical, where $R_a$ is a suitable substituent as defined below.

A "sulfonyl group" is intended to mean a —$SO_2R_a$ radical, where $R_a$ is a suitable substituent as defined below.

A "hydroxy group" is intended to mean the radical —OH.

An "amino group" is intended to mean the radical —$NH_2$.

An "alkylamino group" is intended to mean the radical —$NHR_a$, where $R_a$ is an alkyl group.

A "dialkylamino group" is intended to mean the radical —$NR_aR_b$, where $R_a$ and $R_b$ are each independently an alkyl group.

An "alkoxy group" is intended to mean the radical —$OR_a$, where $R_a$ is an alkyl group. Exemplary alkoxy groups include methoxy, ethoxy, propoxy, and the like.

An "alkoxycarbonyl group" is intended to mean the radical —C(O)$OR_a$, where $R_a$ is an alkyl group.

An "alkylsulfonyl group" is intended to mean the radical —$SO_2R_a$, where $R_a$ is an alkyl group.

An "alkylaminocarbonyl group" is intended to mean the radical —C(O)$NHR_a$, where $R_a$ is an alkyl group.

A "dialkylaminocarbonyl group" is intended to mean the radical —C(O)$NR_aR_b$, where $R_a$ and $R_b$ are each independently an alkyl group.

A "mercapto group" is intended to mean the radical —SH.

An "alkylthio group" is intended to mean the radical —$SR_a$, where $R_a$ is an alkyl group.

A "carboxy group" is intended to mean the radical —C(O)OH.

A "carbamoyl group" is intended to mean the radical —C(O)$NH_2$.

An "aryloxy group" is intended to mean the radical —$OR_c$, where $R_c$ is an aryl group.

A "heteroaryloxy group" is intended to mean the radical —$OR_d$, where $R_d$ is a heteroaryl group.

An "arylthio group" is intended to mean the radical —$SR_c$, where $R_c$ is an aryl group.

A "heteroarylthio group" is intended to mean the radical —$SR_d$, where $R_d$ is a heteroaryl group.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wutz, Protecting Groups in Organic Synthesis, $2^{nd}$ edition, John Wiley and Sons, New York, N.Y. (1991).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxy groups, carboxy groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" is intended to mean any suitable substituent that may be recognized or selected, such as through routine testing, by those skilled in the art. Illustrative examples of useful substituents are those found in the exemplary compounds that follow, as well as halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl; aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O. All of these substituents may optionally be further substituted with a substituent selected from groups such as hydroxy groups, halogens, oxo groups, alkyl groups, acyl groups, sulfonyl groups, mercapto groups, alkylthio groups, alkyloxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroaryloxy groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It is understood that while a chemosensitizing agent of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the chemosensitizing agents may exist as single stereoisomers (i.e., essentially free of other stereoisomers), racemates, or mixtures of enantiomers, diastereomers, or both. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, if the compounds of the present invention are made synthetically, they are used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the invention also include active tautomeric and stereoisomeric forms of the chemosensitizing agents of the Structural Formula A, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

The compounds of the invention were synthesized according to the following scheme:

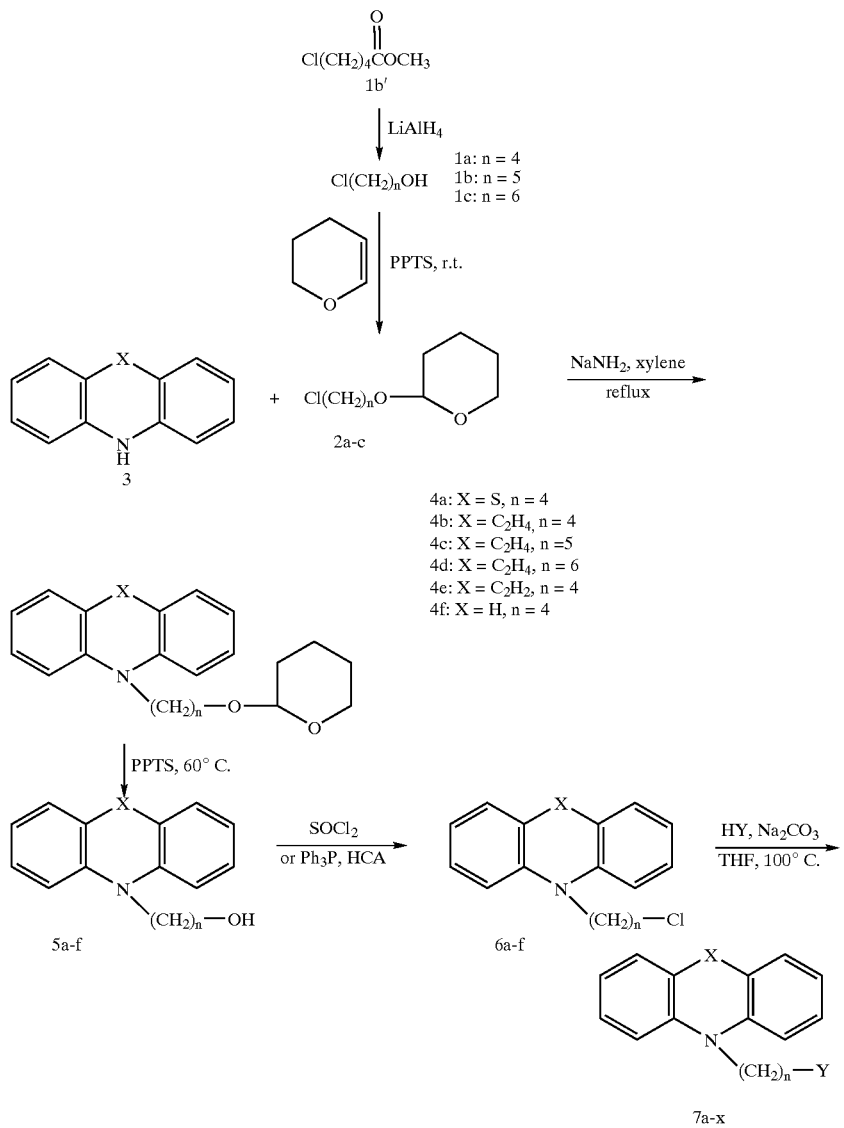

The present invention also includes the above intermediate compounds.

Generally, as schematically illustrated above, the hydroxyl groups of the starting material 4-chloro-1-butanol (1a) and 6-chloro-1-hexanol (1c) were protected by forming tetrahydropyran acetal (THP, 2) using pyridium p-toluenesulfonate (PPTS) as a catalyst. Five-carbon side chain 5-chloro-1-pentanol (1b) was prepared from its corresponding ester, methyl 5-chlorovalerate (1b') by LiAlH$_4$ reduction of the ester group to give the starting alcohol (1b).

A key step to the synthesis of the compounds of the present invention is the conjugation of aliphatic amine side chain with ring nucleus. Phenothiazine and related heterocyclic rings failed to react with alkyl halides due to poor basicity of the ring nitrogen. However, N-alkylation was accomplished under the sodium amide catalysis. The general procedure for the preparation of the N-alkyl derivatives involved salt formation of the ring nitrogen with NaNH$_2$, followed by condensation of the sodium salt with requisite alkyl halides (2a–c) in anhydrous xylene under reflux to afford the conjugates (4a–f) in 20–80% yields, depending on the aromatic rings used.

The THP protecting group was easily removed to give the alcohol (5a–f) at 60° C. The hydroxyl group was converted to the corresponding chloride (6a–b) by treatment of the alcohol with thionyl chloride. In some instances, thionyl chloride failed to provide a satisfactory yield. An alternative method for chlorination using hexachloroacetone (HCA)/triphenylphosphine (Ph$_3$P) afforded compounds 6c–f in yields ranging from 60% to 90%. See Magid, R. M. et al. (1981) *J. Org. Chem.* 46:824–825, which is herein incorporated by reference. Treatment of compounds 6a–f with appropriate amines in the presence of sodium carbonate gave the final products, compounds 7a–x, in 25–93% yields.

Specifically, the compounds of the present invention were synthesized as follows:

To prepare 5-chloro-1-pentanol (1b) a solution of methyl 5-chlorovalerate (180 mg, 1.2 mmol) in 4 ml anhydrous diethyl ether was added dropwise LiAlH$_4$ (1.2 ml, 1.3 mmol, 1M in THF). After 1 hour, the excess of LiAlH$_4$ was decomposed by adding ice-cold diluted sulphuric acid and the white solid was removed by filtration. The filtrate was extracted with ether three times. The ether extracts were combined, dried over anhydrous sodium sulfate, concentrated, and chromatrographed on a column of silica gel. Elution with 10% ethyl acetate/hexanes afforded 146 mg (100%) of colorless liquid (1b). $^1$H NMR (CDCl$_3$, 600 Hz) δ3.68 (2H, t), 3.57 (2H, t), 1.84 (2H, m), 1.61 (2H, m), 1.54 (2H, m); MS (m/z) 121, 105. Anal. (C$_5$H$_{11}$OCl) C, H.

In the synthesis protocols described herein, the hexanes used were purchased from Fisher Chemicals, Catalog Number H292-4, and comprises 86.1% n-hexane, 9.7% methylcyclopentane, and 4.2% of various methylpentanes.

To prepare compounds 2a, 2b, or 2c, a mixture of 1a (0.54 g, 5 mmol), 1b, or 1c, and dihydropyran (0.76 g, 6 mmol) in 15 ml of CH$_2$Cl$_2$ was added PPTS (110 mg, 0.4 mmol). After stirring at room temperature overnight, the mixture was washed with water, dried, concentrated and chromatrographed on a column of silica gel. Elution with 10% ethyl acetate/hexanes afforded the following:

2-(4-Chlorobutyloxy)tetrahydropyran (2a): yield 0.96 g (99%): $^1$H NMR (CDCl$_3$, 600 Hz) δ4.57 (1H, s), 3.86–3.75 (2H, m), 3.59–3.41 (4H, m), 1.91–1.51 (10H, m); MS (m/z) 193, 157, 103. Anal. (C$_9$H$_{17}$O$_2$Cl) C, H.

2-(5-Chloropentyloxy)tetrahydropyran (2b): yield 98%, $^1$H NMR (CDCl$_3$, 300 Hz) δ4.57 (1H, s), 3.89–3.71 (2H, m), 3.56–3.35 (4H, m), 1.86–1.47 (12H, m); MS (m/z) 207, 105. Anal. (C$_{10}$H$_{19}$O$_2$Cl.0.25H$_2$O) C, H.

2-(6-Chlorohexyloxy)tetrahydropyran (2c): yield 97%, $^1$H NMR (CDCl$_3$, 600 Hz) δ4.60 (1H, s), 3.89–3.75 (2H, m), 3.57–3.40 (4H, m), 1.84–1.43 (14H, m); MS (m/z) 221, 119, 101. Anal. (C$_{11}$H$_{21}$O$_2$Cl) C, H.

To prepare compounds 4a–f, a reaction mixture containing phenothiazine (2.1 g, 10.5 mmol) and sodium amide (0.46 g, 12 mmol) in anhydrous xylenes was refluxed for 2 hours. After the mixture was cooled to room temperature, compound 2a (2.26 g, 12 mmol), 2b, or 2c was added and the mixture was refluxed for 6 hours. Ice water was added dropwise to quench excess sodium amide. The mixture was filtered, washed with water, dried and concentrated. The residue was purified via silica gel column eluting with 5% ethyl acetate/hexanes to afford the following:

10-[4-(Tetrahydropyran-2-yloxy)-butyl]-10H-phenothiazine (4a): yield 1.46 g (46%). $^1$H NMR (CDCl$_3$, 600 Hz) δ7.17 (4H, m), 6.92 (4H, m), 4.56 (1H, s), 3.94 (2H, t), 3.88–3.76 (2H, m), 3.53–3.42 (2H, m), 1.94–1.52 (10H, m); MS (m/z) 355 (M$^+$), 272, 200. Anal. (C$_{21}$H$_{25}$O$_2$NS) C, H, N.

N-[4-(Tetrahydropyran-2-yloxy)-butyl]iminodibenzyl (4b): yield 31%, $^1$H NMR (CDCl$_3$, 600 Hz) δ7.15 (6H, m), 6.95 (2H, t), 4.55 (1H, s), 3.84–3.71 (4H, m), 3.50–3.39 (2H, m), 3.20 (4H, s), 1.71–1.51 (10H, m); MS (m/z) 351 (M$^+$), 268, 250, 196. Anal. (C$_{23}$H$_{29}$O$_2$N) C, H, N.

N-[5-(Tetrahydropyran-2-yloxy)-pentyl]iminodibenzyl (4c): yield 64%, $^1$H NMR (CDCl$_3$, 600 Hz) δ7.14 (6H, m), 6.94 (2H, t), 4.57 (1H, s), 3.86–3.71 (4H, m), 3.87–3.70 (2H, m), 3.20 (4H, s), 1.71–1.44 (12H, m); MS (m/z) 366 (MH$^+$), 282, 264, 208. Anal. (C$_{24}$H$_{31}$O$_2$N) C, H, N.

N-[6-(Tetrahydropyran-2-yloxy)-hexyl]iminodibenzyl (4d): yield 81%, $^1$H NMR (CDCl$_3$, 600 Hz) δ7.14 (6H, m), 6.94 (2H, t), 4.57 (1H, s), 3.89–3.70 (4H, m), 3.52–3.35 (2H, m), 3.19 (4H, s), 1.85–1.34 (14H, m); MS (m/z) 380 (MH$^+$), 296, 208. Anal. (C$_{25}$H$_{33}$O$_2$N.0.5H$_2$O) C, H, N.

N-[4-(Tetrahydropyran-2-yloxy)-butyl]iminostilbene (4e): yield 60%, $^1$H NMR (CDCl$_3$, 300 Hz) δ7.24 (2H, m), 7.06–6.94 (6H, m), 6.71 (2H, s), 4.49 (1H, s), 3.82–3.63 (4H, m), 3.47–3.32 (2H, m), 1.77–1.46 (10H, m); MS (m/z) 349 (M$^+$), 266, 248, 194. Anal. (C$_{23}$H$_{27}$O$_2$N) C, H, N.

Diphenyl-[4-(tetrahydropyran-2-yloxy)-butyl]-amine (4f): yield 55%, $^1$H NMR (CDCl$_3$, 600 Hz) δ7.29 (4H, t), 7.0 (4H, d), 6.97 (2H, t), 4.59 (1H, s), 3.87–3.75 (4H, m), 3.52–3.42 (2H, m), 1.80–1.54 (10H, m); MS (m/z) 325 (M$^+$), 270, 242, 224. Anal. (C$_{21}$H$_{27}$O$_2$N) C, H, N.

To prepare compounds 5a–f, PPTS (14 mg, 0.056 mmol) was added to the solution of 4a (214 mg, 0.56 mmol), 4b, 4c, 4d, 4e, or 4f in 10 ml mixture of methanol/THF (1:1). The reaction mixture was heated up to 60° C. for 4 hours. After solvent evaporation, the residue was dissolved in 10 ml of CH$_2$Cl$_2$, washed with water, dried, and concentrated. The crude oil was chromatographed on silica gel column. Elution with 2% CH$_3$OH/CH$_2$Cl$_2$ afforded the following compounds:

4-Phenothiazine-10-yl-butan-1-ol (5a): yield 153 mg (100%). $^1$H NMR (CDCl$_3$, 300 Hz) δ7.16 (4H, m), 6.89 (4H, m), 3.90 (2H, t), 3.63 (2H, t), 1.86 (2H, m), 1.68 (2H, m); MS (m/z) 271 (M$^+$), 254, 200. Anal. (C$_{16}$H$_{17}$ONS.0.25H$_2$O) C, H, N.

4-Iminodibenzyl-butan-1-ol (5b): yield 73%, $^1$H NMR (CDCl$_3$, 300 Hz) δ7.09 (6H, m), 6.92 (2H, m), 3.75 (2H, t), 3.60 (2H, t), 3.17 (4H, s), 1.70–1.54 (4H, m); MS (m/z) 268 (MH$^+$), 250, 196. Anal. (C$_{18}$H$_{21}$ON) C, H, N.

5-Iminodibenzyl-pentan-1-ol (5c): yield 91%, $^1$H NMR (CDCl$_3$, 300 Hz) δ7.09 (6H, m), 6.89 (2H, m), 3.74 (2H, t), 3.57 (2H, t), 3.17 (4H, s), 1.69–1.32 (6H, m); MS (m/z) 282 (MH$^+$), 264, 208. Anal. (C$_{19}$H$_{23}$ON) C, H, N.

6-Iminodibenzyl-hexan-1-ol (5d): yield 83%, $^1$H NMR (CDCl$_3$, 300 Hz) δ7.08 (6H, m), 6.90 (2H, m), 3.72 (2H, t), 3.58 (2H, t), 3.16 (4H, s), 1.62–1.26 (8H, m); MS (m/z) 296(MH$^+$), 278, 208. Anal. (C$_{20}$H$_{25}$ON.0.25H$_2$O) C, H, N.

4-Iminostilbene-butan-1-ol (5e): yield 68%, $^1$H NMR (CDCl$_3$, 300 Hz) δ7.26 (2H, m), 7.03 (6H, m), 6.75 (2H, s), 3.76 (2H, t), 3.57 (2H, t), 1.78–1.57 (4H, m); MS (m/z) 266 (MH$^+$), 248, 194. Anal. (C$_{18}$H$_{19}$ON.0.25 CH$_3$CO$_2$C$_2$H$_5$) C, H, N.

4-Diphenylamino-butan-1-ol (5f): yield 78%, $^1$H NMR (CDCl$_3$, 300 Hz) δ7.26 (4H, m), 6.98 (6H, m), 3.78 (2H, t), 3.67 (2H, t), 1.80–1.55 (4H, m); MS (m/z) 242 (MH$^+$), 224, 170. Anal. (C$_{16}$H$_{19}$ON) C, H, N.

To prepare compounds 6a, 6b and 6e, to a solution of 5a (2.03 g, 7.5 mmol), 5b or 5e in 100 ml of dry benzene was added thionyl chloride (2 ml, 10 mmol) and stirred overnight at room temperature. After solvent evaporation, the residue was chromatographed on silica gel column. Elution with 10% ethyl acetate/hexanes afforded the following compounds:

10-(4-Chlorobutyl)phenothiazine (6a): yield 2.17 g (62%). $^1$H NMR (CDCl$_3$, 300 Hz) δ7.16 (4H, m), 6.89 (4H, m), 3.89 (2H, t), 3.54 (2H, t), 2.02–1.85 (4H, m); MS (m/z) 290 (M$^+$), 254, 212, 199. Anal. (C$_{16}$H$_{16}$NS) C, H, N.

5-(4-Chlorobutyl)iminodibenzyl (6b): yield 62%, $^1$H NMR (CDCl$_3$, 300 Hz) δ7.15 (6H, m), 6.98 (2H, m), 3.81 (2H, t), 3.53 (2H, t), 3.21 (4H, s), 1.90–1.67 (4H, m); MS (m/z) (m/z) 286 (M$^+$), 250, 208. Anal. (C$_{18}$H$_{20}$NCl) C, H, N.

5-(4-Chlorobutyl)iminostilbene (6e): yield 80%, $^1$H NMR (CDCl$_3$, 300 Hz) δ7.26 (2H, m), 7.02 (6H, m), 6.72 (2H, s), 3.75 (2H, t), 3.48 (2H, t), 1.85 (2H, m), 1.70 (2H, m); MS (m/z) 284 (M$^+$), 248, 206. Anal. (C$_{18}$H$_{18}$NCl) C, H, N.

To prepare compounds 6c, 6d and 6f to a cooled 25 ml round-bottomed flask containing 5c (50 mg, 0.16 mmol), 5d or 5f and Ph$_3$P (51 mg, 0.2 mmol) was added HCA (0.05 ml, 0.3 mmol) in 1 ml CH$_2$Cl$_2$. The reaction mixture was allowed to come to room temperature and stirred overnight. Flash silica gel column chromatography by eluting with hexane to remove the HCA followed by 5% ethyl acetate/hexanes afforded the following compounds:

5-(5-Chloropentyl)iminodibenzyl (6c): yield 49 mg (93%). $^1$H NMR (CDCl$_3$, 600 Hz) δ7.14 (6H, m), 6.96 (2H, m), 3.78 (2H, t), 3.51 (2H, t), 3.20 (4H, s), 1.76 (2H, m), 1.62 (2H, m), 1.52 (2H, m); MS (m/z) 300 (M$^+$), 264, 208. Anal. (C$_{19}$H$_{22}$NCl) C, H, N.

5-(6-Chlorohexyl)iminodibenzyl (6d): yield 100%, $^1$H NMR (CDCl$_3$, 600 Hz) δ7.14 (6H, m), 6.95 (2H, m), 3.77 (2H, t), 3.51 (2H, t), 3.20 (4H, s), 1.73 (2H, m), 1.61 (2H, m), 1.40 (4H, m); MS (m/z) 314 (M$^+$), 278, 208. Anal. (C$_{20}$H$_{24}$NCl) C, H, N.

4-Chlorobutyl-diphenylamine (6f): yield 65%, $^1$H NMR (CDCl$_3$, 300 Hz) δ7.26 (4H, m), 6.97 (6H, m), 3.74 (2H, t), 3.54 (2H, t), 1.82 (4H, m); MS (m/z) 260 (M$^+$), 224, 182. Anal. (C$_{16}$H$_{18}$NCl.0.25H$_2$O) C, H, N.

To prepare compounds 7a–x, to a solution of 6a (125 mg, 0.4 mmol), 6b, 6c, 6d, 6e, 6f, 6g, 6h, 6i, 6j, 6k, 6l, 6m, 6n, 6o, 6p, 6q, 6r, 6s, 6t, 6u, 6v, 6w, or 6x in 1 ml of THF was added 1 ml of dimethylamine (30% in H$_2$O) and a catalytic amount of Na$_2$CO$_3$. The mixture was heated to 100° C. in a sealed tube for 24 hours. The reaction mixture was filtered, diluted with water, extracted with ethyl acetate, dried and concentrated. The crude oil was chromatographed on silica gel column. Eluting with 2% CH$_3$OH/CH$_2$Cl$_2$ afforded the following compounds:

10-(4-Dimethylaminobutyl)phenothiazine (7a): yield 56 mg (44%). $^1$H NMR (CDCl$_3$, 300 Hz) δ7.13 (4H, m), 6.88 (4H, m), 3.87 (2H, t), 2.26 (2H, t), 2.17 (6H, s), 1.83 (2H, m), 1.59 (2H, m); MS (m/z) 298 (M$^+$), 254, 200, 100. Anal. (C$_{18}$H$_{22}$N$_2$S. 0.25CH$_3$CO$_2$C$_2$H$_5$) C, H, N.

10-(4-Diethylaminobutyl)phenothiazine (7b): yield 53%, $^1$H NMR (CDCl$_3$, 300 Hz) δ7.13 (4H, m), 6.88 (4H, m), 3.87 (2H, t), 2.47 (6H, m), 1.81 (2H, m), 1.59 (2H, m), 0.98 (6H, s); MS (m/z) 326(M$^+$), 311, 254, 128. Anal. (C$_{20}$H$_{26}$N$_2$S.0.25H$_2$O) C, H, N.

10-(4-Methylbenzylaminobutyl)phenothiazine (7c): yield 86%, $^1$H NMR (CDCl$_3$, 300 Hz) δ7.26 (5H, m), 7.14 (4H, m), 6.88 (4H, m), 3.86 (2H, t), 3.50 (2H, s), 2.43 (2H, t), 2.18 (3H, s), 1.85 (2H, m), 1.68 (2H, m); MS (m/z) 375(MH$^+$), 176. Anal. (C$_{24}$H$_{26}$N$_2$S.0.25H$_2$O) C, H, N.

10-(4-Dibenzylaminobutyl)phenothiazine (7d): yield 92%, $^1$H NMR (CDCl$_3$, 300 Hz) δ7.26 (10H, m), 7.10 (4H, m), 6.88 (2H, t), 6.76 (2H, t), 3.73 (2H, t), 3.50 (4H, s), 2.41 (2H, t), 1.79(2H, m), 1.63 (2H, m); MS (m/z) 451 (MH$^+$), 252. Anal. (C$_{30}$H$_{30}$N$_2$S. 0.25CH$_3$CO$_2$C$_2$H$_5$) C, H, N.

10-(4-Pyrrolidin-1-yl-butyl)phenothiazine (7e): Yield 34%, $^1$H NMR (CDCl$_3$, 300 Hz) δ7.13 (4H, m), 6.88 (4H, m), 3.87 (2H, t), 2.45 (6H, m), 1.85 (2H, m), 1.74 (4H, m), 1.64 (2H, m); MS (m/z) 324 (M$^+$),126. Anal. (C$_{20}$H$_{24}$N$_2$S) C, H, N.

10-(4-Piperidin-1-yl-butyl)phenothiazine (7f): Yield 75%, $^1$H NMR (CDCl$_3$, 300 Hz) δ7.13 (4H, m), 6.88 (4H, m), 3.85 (2H, t), 2.30 (6H, t), 1.83 (2H, m), 1.64 (2H, m), 1.58 (4H, m), 1.42 (2H, m); MS (m/z) 338 (M$^+$), 140. Anal. (C$_{21}$H$_{26}$N$_2$S. 0.25CH$_3$CO$_2$C$_2$H$_5$) C, H, N.

10-(4-Morpholin-4-yl-butyl)phenothiazine (7g): yield 73%, $^1$H NMR (CDCl$_3$, 300 Hz) δ7.14 (4H, m), 6.89 (4H, m), 3.88 (2H, t), 3.64 (4H, t), 2.33 (6H, t), 1.85 (2H, m), 1.61 (2H, m); MS (m/z) 340 (M$^+$),142. Anal. (C$_{20}$H$_{24}$N$_2$SO) C, H, N.

10-[4-(4-Methyl-piperazin-1-yl)-butyl]phenothiazine (7h): yield 31%, $^1$H NMR (CDCl$_3$, 300 Hz) δ7.14 (4H, m), 6.89 (4H, m), 3.87 (2H, t), 2.35 (10H, m), 2.27 (3H, s), 1.84 (2H, m), 1.62 (2H, m); MS (m/z) 354 (MH$^+$),155. Anal. (C$_{21}$H$_{27}$N$_3$S.1H$_2$O) C, H, N.

5-(4-Dimethylaminobutyl)iminodibenzyl (7i): Yield 54%, $^1$H NMR (CDCl$_3$, 300 Hz) δ7.10 (6H, m), 6.91 (2H, m), 3.74 (2H, t), 3.15 (4H, s), 2.22 (2H, t), 2.18 (6H, s), 1.55 (4H, m); MS (m/z) 294 (M$^+$), 100. Anal. (C$_{20}$H$_{26}$N$_2$.0.25H$_2$O) C, H, N.

5-(4-Diethylaminobutyl)iminodibenzyl (7j): Yield 42%, $^1$H NMR (CDCl$_3$, 300 Hz) δ7.10 (6H, m), 6.90 (2H, m), 3.74 (2H, t), 3.16 (4H, s), 2.45 (4H, q), 2.34 (2H, t), 1.52 (4H, m), 0.95 (6H, t); MS (m/z) 322 (M$^+$), 128. Anal. (C$_{22}$H$_{30}$N$_2$) C, H, N.

5-(4-Methylbenzylaminobutyl)iminodibenzyl (7k): Yield 93%, $^1$H NMR (CDCl$_3$, 300 Hz) δ7.23 (5H, m), 7.05 (6H, m), 6.89 (2H, t), 3.65 (2H, t), 3.41 (2H, s), 3.20 (4H, s), 2.28 (2H, t), 2.16 (3H, s), 1.52 (4H, m); MS (m/z) 370 (M$^+$), 176. Anal. (C$_{26}$H$_{30}$N$_2$. 0.25CH$_3$CO$_2$C$_2$H$_5$) C, H, N.

5-(4-Dibenzylaminobutyl)iminodibenzyl (7l): Yield 46%, $^1$H NMR (CDCl$_3$, 300 Hz) δ7.23 (10H, m), 7.05 (6H, m), 6.89 (2H, t), 3.62 (2H, t), 3.46 (4H, s), 3.13 (4H, s), 2.33 (2H, t), 1.52 (4H, m); MS (m/z) 447 (MH$^+$), 355, 252. Anal. (C$_{32}$H$_{34}$N$_2$.0.5H$_2$O) C, H, N.

5-(4-Pyrrolidin-1-yl-butyl)iminodibenzyl (7m): Yield 44%, $^1$H NMR (CDCl$_3$, 300 Hz) δ7.09 (6H, m), 6.90 (2H, m), 3.74 (2H, t), 3.16 (4H, s), 2.39 (6H, m), 1.73 (4H, m), 1.57 (4H, m); MS (m/z) 320 (M$^+$), 126. Anal. (C$_{22}$H$_{28}$N$_2$.0.25H$_2$O) C, H, N.

5-(4-Piperidin-1-yl-butyl) iminodibenzyl (7n): Yield 75%, $^1$H NMR (CDCl$_3$, 600 Hz) δ7.13 (6H, m), 6.94 (2H, m), 3.77 (2H, t), 3.20 (4H, s), 2.28 (6H, m), 1.58 (10H, m); MS (m/z) 334(M$^+$), 140. Anal. (C$_{23}$H$_{30}$N$_2$) C, H, N.

5-(4-Morpholin-4-yl-butyl)iminodibenzyl (7o): Yield 88%, $^1$H NMR (CDCl$_3$, 300 Hz) δ7.09 (6H, m), 6.90 (2H, m), 3.74 (2H, t), 3.64 (4H, t), 3.15 (4H, s), 2.32 (4H, t), 2.25 (2H, t), 1.55 (4H, m); MS (m/z) 336 (M$^+$), 142. Anal. (C$_{22}$H$_{28}$N$_2$O) C, H, N.

5-[4-(4-Methyl-piperazin-1-yl)-butyl]iminodibenzyl (7p): Yield 72%, $^1$H NMR (CDCl$_3$, 300 Hz) δ7.09 (6H, m), 6.90 (2H, m), 3.73 (2H, t), 3.15 (4H, s), 2.36 (10H, m), 2.26 (3H, s), 1.54 (4H, m); MS (m/z) 349 (M$^+$), 155. Anal. (C$_{23}$H$_{31}$N$_3$.0.25H$_2$O) C, H, N.

5-(4-Diethylaminobutyl)iminostilbene (7q): Yield 61%, $^1$H NMR (CDCl$_3$, 300 Hz) δ7.24 (2H, m), 7.00 (6H, m), 6.71 (2H, s), 3.72 (2H, t), 2.45 (4H, q), 2.35 (2H, t), 1.52 (4H, m), 0.95 (6H, t); MS (m/z) 320 (M$^+$), 128. Anal. (C$_{22}$H$_{28}$N$_2$) C, H, N.

5-(4-Pyrrolidin-1-yl-butyl)iminostilbene (7r): Yield 48%, $^1$H NMR (CDCl$_3$, 300 Hz) δ7.24 (2H, m), 7.00 (6H, m), 6.71 (2H, s), 3.72 (2H, t), 2.40 (6H, m), 1.73 (4H, m), 1.60 (4H, m); MS (m/z) 319 (MH$^+$), 126. Anal. (C$_{22}$H$_{26}$N$_2$.0.25H$_2$O) C, H, N.

N,N-Diethyl-N',N'-diphenyl-butane-1,4-diamine (7s): Yield 40%, $^1$H NMR (CDCl$_3$, 300 Hz) δ7.25 (4H, m), 6.96 (6H, m), 3.71 (2H, t), 2.51 (4H, q), 2.42 (2H, t), 1.65 (2H, m), 1.50 (2H, m), 1.00 (6H, t); MS (m/z) 297 (MH$^+$), 224, 128. Anal. (C$_{20}$H$_{28}$N$_2$. 0.25H$_2$O) C, H, N.

Diphenyl-(4-pyrrolidin-1-yl-butyl)amine (7t): Yield 25%, $^1$H NMR (CDCl$_3$, 300 Hz) δ7.25 (4H, m), 6.96 (6H, m), 3.71 (2H, t), 2.51 (4H, m), 2.47 (2H, t), 1.79 (4H, m), 1.70 (2H, m), 1.58 (2H, m); MS (m/z) 294 (M$^+$), 126. Anal. (C$_{20}$H$_{26}$N$_2$. 0.25CH$_3$CO$_2$C$_2$H$_5$) C, H, N.

5-(5-Diethylaminopentyl)iminodibenzyl (7u): Yield 29%, $^1$H NMR (CDCl$_3$, 300 Hz) δ7.08 (6H, m), 6.90 (2H, m), 3.72 (2H, t), 3.15 (4H, s), 2.47 (4H, q), 2.33 (2H, t), 1.30~1.62 (6H, m), 0.97 (6H, t); MS (m/z) 337 (MH$^+$). Anal. (C$_{23}$H$_{32}$N$_2$.0.25H$_2$O) C, H, N.

5-(5-Pyrrolidin-1-yl-pentyl)iminodibenzyl (7v): Yield 50%, $^1$H NMR (CDCl$_3$, 300 Hz) δ7.08 (6H, m), 6.89 (2H, m), 3.72 (2H, t), 3.15 (4H, s), 2.44 (4H, m), 2.36 (2H, t), 1.74 (4H, m), 1.28~1.62 (6H, m); MS (m/z) 335 (MH$^+$), 140. Anal. (C$_{23}$H$_{30}$N$_2$. 0.25CH$_3$CO$_2$C$_2$H$_5$) C, H, N.

5-(6-Diethylaminohexyl)iminodibenzyl (7w): yield 36%, $^1$H NMR (CDCl$_3$, 300 Hz) δ7.10 (6H, m), 6.90 (2H, m), 3.71 (2H, t), 3.15 (4H, s), 2.62 (4H, q), 2.47 (2H, t), 1.20~1.60 (8H, m), 1.05 (6H, t); MS (m/z) 351 (MH$^+$). Anal. (C$_{24}$H$_{34}$N$_2$.0.25H$_2$O) C, H, N.

5-(6-Pyrrolidin-1-yl-hexyl)iminodibenzyl (7x): yield 45%, $^1$H NMR (CDCl$_3$, 300 Hz) δ7.09 (6H, m), 6.89 (2H, m), 3.71 (2H, t), 3.15 (4H, s), 2.44 (4H, m), 2.34 (2H, t), 1.75 (4H, m), 1.20~1.60 (8H, m); MS (m/z) 349 (MH$^+$). Anal. (C$_{24}$H$_{32}$N$_2$.0.25H$_2$O) C, H,N.

Proton nuclear magnetic resonance ($^1$H NMR) spectra were measured on a Bruker AC-300 or Avance-600 spectrometer with Me$_4$Si (TMS) as the internal reference. Elemental analysis were performed by Atlantic Microlab Inc. (Norcross, Ga.) where analysis are indicated by symbols of the elements, the analytical results obtained were within ±0.4% of the theoretical values. Mass spectra were recorded on a Finnigan LCQ mass spectrometer. Silica gel (70–230 mesh), from EM, was used for column chromatography.

Table 1 shows the elemental analysis of each of the compounds of the present invention.

TABLE 1

Elemental Analysis

| compd | Theory | | | Found | | |
|---|---|---|---|---|---|---|
| | C | H | N | C | H | N |
| 1b | 48.99 | 9.04 | | 49.03 | 9.12 | |
| 2a | 56.10 | 8.89 | | 55.88 | 8.91 | |
| 2b | 56.87 | 9.31 | | 56.81 | 9.03 | |
| 2c | 59.85 | 9.59 | | 59.55 | 9.58 | |
| 4a | 70.95 | 7.09 | 3.94 | 70.84 | 7.13 | 4.00 |
| 4b | 78.60 | 8.32 | 3.98 | 78.64 | 8.29 | 3.99 |
| 4c | 78.87 | 8.55 | 3.83 | 78.60 | 8.67 | 3.82 |
| 4d | 77.28 | 8.82 | 3.60 | 76.99 | 8.96 | 3.34 |
| 4e | 79.05 | 7.79 | 4.01 | 78.95 | 7.81 | 4.04 |
| 4f | 77.50 | 8.36 | 4.30 | 77.42 | 8.37 | 4.34 |
| 5a | 69.66 | 6.39 | 5.08 | 69.76 | 6.37 | 5.06 |
| 5b | 80.86 | 7.92 | 5.24 | 80.62 | 8.06 | 5.21 |
| 5c | 81.10 | 8.24 | 4.98 | 81.08 | 8.32 | 4.95 |
| 5d | 80.09 | 8.57 | 4.67 | 79.92 | 8.49 | 4.66 |
| 5e | 79.41 | 7.37 | 4.87 | 79.25 | 7.71 | 4.82 |
| 5f | 79.63 | 7.94 | 5.80 | 79.36 | 7.74 | 5.80 |
| 6a | 66.31 | 5.56 | 4.83 | 66.14 | 5.56 | 4.87 |
| 6b | 75.64 | 7.05 | 4.90 | 75.64 | 6.87 | 4.86 |
| 6c | 76.11 | 7.40 | 4.67 | 75.84 | 7.44 | 4.66 |
| 6d | 76.54 | 7.71 | 4.46 | 76.77 | 7.79 | 4.45 |
| 6e | 76.18 | 6.39 | 4.94 | 76.11 | 6.64 | 4.69 |
| 6f | 72.72 | 7.06 | 5.30 | 72.91 | 7.07 | 5.16 |
| 7a | 71.21 | 7.55 | 8.74 | 71.54 | 7.82 | 8.38 |
| 7b | 72.57 | 8.07 | 8.46 | 72.65 | 8.02 | 8.27 |
| 7c | 76.05 | 7.05 | 7.39 | 76.29 | 7.03 | 7.20 |
| 7d | 78.77 | 6.82 | 5.93 | 78.92 | 6.75 | 5.95 |
| 7e | 74.03 | 7.45 | 8.63 | 73.78 | 7.57 | 8.38 |
| 7f | 73.29 | 7.83 | 7.77 | 73.69 | 7.94 | 7.65 |
| 7g | 70.55 | 7.10 | 8.23 | 70.35 | 7.06 | 8.15 |
| 7h | 67.89 | 7.87 | 11.31 | 67.83 | 7.71 | 11.12 |
| 7i | 80.36 | 8.93 | 9.37 | 80.24 | 8.85 | 9.21 |
| 7j | 81.94 | 9.38 | 8.69 | 81.91 | 9.40 | 8.53 |
| 7k | 82.61 | 8.22 | 7.14 | 82.84 | 8.11 | 7.27 |
| 7l | 84.35 | 7.74 | 6.15 | 84.72 | 7.79 | 6.15 |
| 7m | 81.31 | 8.84 | 8.62 | 81.50 | 8.80 | 8.55 |
| 7n | 82.59 | 9.04 | 8.37 | 82.29 | 9.08 | 8.23 |
| 7o | 78.53 | 8.39 | 8.33 | 78.28 | 8.42 | 8.17 |
| 7p | 78.03 | 8.97 | 11.87 | 78.40 | 9.04 | 11.57 |
| 7q | 82.45 | 8.81 | 8.74 | 82.28 | 9.00 | 8.45 |
| 7r | 81.82 | 8.27 | 8.67 | 81.75 | 8.16 | 8.66 |
| 7s | 79.82 | 9.54 | 9.31 | 80.19 | 9.42 | 9.22 |
| 7t | 79.70 | 8.92 | 8.85 | 79.85 | 8.79 | 9.07 |
| 7u | 81.01 | 9.61 | 8.21 | 80.72 | 9.60 | 7.81 |
| 7v | 79.32 | 9.05 | 7.40 | 79.31 | 9.06 | 7.40 |
| 7w | 81.19 | 9.79 | 7.89 | 81.20 | 9.66 | 7.69 |
| 7x | 81.65 | 9.28 | 7.94 | 81.36 | 9.17 | 7.71 |

The in vitro anti-MDR effects of phenothiazine derivatives on chloroquine and mefloquine resistant TM91C235 cell lines were evaluated by cell growth suppression and the results are displayed in Table 2.

For quantitative in vitro drug susceptibility testing, two well characterized *P. falciparum* clones, W2 and D6, were used. See Oduola et al. (1988) *Exp Parasitol* 66:86–95, which is herein incorporated by reference. W2 is a clone of the Indochina I isolate and is resistant to chloroquine and pyrimethamine, but susceptible to mefloquine. D6 is a clone from the Sierra I/UNC isolate and is susceptible to chloroquine and pyrimethamine, but has reduced susceptibilities to mefloquine and halofantrine. TM91C235 was isolates from Thailand and is highly resistant to mefloquine, chloroquine, and quinine.

In Vitro Drug Susceptibility Methods

The in vitro antimalarial drug susceptibility assay used is a modification of the procedures first published by Desjardins, et al. with modifications developed by Milhous, et al. See Desjardins, R. E., et al. (1979) *Antimicrobial*

Agents Chemother 16:710–718; and Milhous, et al. (1985) Antimicrobial Agents Chemother 27:525–530, which are herein incorporated by reference. In brief, the assay is based on the incorporation of radiolabeled hypoxanthine by the parasites and inhibition of isotope incorporation is attributed to activity of known or candidate antimalarial drugs. For each assay, proven antimalarials, such as chloroquine, mefloquine, quinine, artemisinin, pyrimethamine and sulfadoxine, were used as controls. The incubation period was 66 hours and the starting parasitemia was 0.2% with a 1% hematocrit. The media used was RPMI-1640 culture media with no folate or p-aminobenzoic acid (PABA). Albumax may be used instead of 10% normal heat inactivated human plasma. The primary difference in Albumax versus human plasma is less protein binding of the drug and, hence, many compounds are slightly more active in this model.

If a candidate compound was tested without any prior knowledge of its activity or solubility, the compound was dissolved directly in dimethylsulfoxide (DMSO) and diluted 400 fold with complete culture media. These unknown compounds were normally started at a highest concentration of about 50,000 ng/ml. The compounds were then diluted 2-fold, 11 times, to give a concentration range of about 1,048-fold. These dilutions were performed automatically by a Biomek 1000 or 2000 Liquid Handling System into 96-well microtiter plates.

25 μl of each diluted candidate compound was then transferred to test plates, 200 μl of parasitized erythrocytes (0.2% parasitemia and 1% hematocrit) were added, and incubated at 37° C. in a controlled environment of 5% $CO_2$, 5% $O_2$ and 90% $N_2$. After 42 hours, 25 μl of $^3$H-hypoxanthine was added and the plates were incubated for an additional 24 hours. At the end of the 66 hour incubation period, the plates were frozen at −70° C. to lyse the red cells and later thawed and harvested onto glass fiber filter mats by using a 96-well cell harvester. The filter mats were then counted in a scintillation counter and the data was analyzed. For each drug, the concentration response profile is determined and 50% inhibitory concentrations ($IC_{50}$) and 90% inhibitory concentrations ($IC_{90}$) are determined by using a nonlinear, logistic dose response analysis program. Evaluation of Chemosensitzing Activity of the New Modulators Fifty percent inhibitory concentrations ($IC_{50s}$) were determined for each candidate compound alone and for candidate compounds in fixed combinations of their respective $IC_{50s}$ (1:1, 1:3, 3:1). These data were used to calculate fractional inhibitory concentration (FICs). See Elion, G. V., et al. (1954) *J Biol Chem* 208:477–488, which is herein incorporated by reference. The FIC is the actual $IC_{50}$ of one compound in the presence of a second compound but is expressed as a fraction of its $IC_{50}$ when used alone. This index is a mathematical representation of the isobologram such that an FIC index of 1.0 represents the line of additive on the isobologram. An FIC index of less than 1.0 represents synergy or potentiation and an FIC index of greater than 1.0 represents antagonism.

TABLE 2

In Vitro Reversal Activity of New Modulators in TM91C235 cells.[1]

| compd | X | Y | $R_1$ | $R_2$ | Control[2] % sup | | | Chloroquine[3] % sup | | | Mefloquine[4] % SUP | | |
|---|---|---|---|---|---|---|---|---|---|---|---|---|---|
| | | | | | 5000* | 500* | 50* | 5000* | 500* | 50* | 5000* | 500* | 50* |
| 7a | S | — | $CH_3$ | $CH_3$ | 92 | 27 | 17 | 100 | 97 | 30 | 92 | 31 | 2 |
| 7b | S | — | $C_2H_5$ | $C_2H_5$ | 100 | 38 | 26 | 100 | 99 | 31 | 100 | 30 | 17 |
| 7c | S | — | $CH_3$ | benzyl | 35 | 18 | 13 | 62 | 27 | 14 | 13 | 0 | 0 |
| 7d | S | — | benzyl | benzyl | 22 | 10 | 7 | 25 | 16 | 12 | 9 | 3 | 0 |
| 7e | S | pyrrolidinyl | — | — | 96 | 70 | 38 | 100 | 99 | 99 | 95 | 67 | 33 |
| 7i | $C_2H_4$ | — | $CH_3$ | $CH_3$ | 96 | 73 | 59 | 100 | 99 | 99 | 95 | 70 | 43 |
| 7j | $C_2H_4$ | — | $C_2H_5$ | $C_2H_5$ | 100 | 95 | 62 | 100 | 100 | 99 | 100 | 95 | 64 |
| 7k | $C_2H_4$ | — | $CH_3$ | benzyl | 60 | 32 | 30 | 33 | 20 | 10 | 41 | 22 | 20 |
| 7l | $C_2H_4$ | — | benzyl | benzyl | 13 | 17 | 11 | 13 | 8 | 6 | 19 | 22 | 14 |
| 7m | $C_2H_4$ | pyrrolidinyl | — | — | 100 | 98 | 58 | 100 | 100 | 99 | 100 | 96 | 64 |

[1]Resistant to both chloroquine and mefloquine.
[2]Test compounds only.
[3]Combination of 10 ng/ml of chloroquine (no effect on cell growth inhibition at this concentration alone) and test compounds.
[4]Combination of 5 ng/ml of mefloquine (no effect on cell growth inhibition at this concentration alone) and test compounds.
*ng/ml Each of these test compounds were tested under three different concentrations, 5000, 500, and 50 ng/ml, in the presence of 10 ng/ml of chloroquine and 5 ng/ml of mefloquine. 10 ng/ml of chloroquine alone at these dose levels and 5 ng/ml of mefloquine alone at these dose levels did not inhibit the cell growth of the TM91C235 cells. Most of the test compounds exhibited MDR modulating activity. For example, compounds 7e, 7i, 7j, and 7m at concentration of about 50 ng/ml completely restored the sensitivity of TM91C235 cells to chloroquine as observed by about 99% cell growth suppression or inhibition. Thus, the compounds of the present invention may be used to treat, prevent or inhibit drug resistant malaria.

The modulating, sensitizing, or reversing activity of the test compounds decreased as the size of the substituent of the terminal amino group increased from diethyl to methybenzyl and dibenzyl in compounds 7c, 7d, 7k, and 7l. Coadministration of compounds 7c and 7d in combination with mefloquine did not significantly improve cell growth suppression or inhibition and are therefore considered to be not very active in restoring the drug sensitivity of the mefloquine resistant cell line.

Some of the compounds of the present invention, 7e, 7i, 7j, and 7m, also exhibited moderate antimalaria activity, about 33% to about 64% cell growth suppression or inhibition, in the absence of chloroquine or mefloquine, thereby indicating that these compounds possess intrinsic antimalarial activity when used alone. Therefore, the compounds of the present invention may also be used alone or in combination with other antimalarial drugs to treat, prevent, or inhibit malaria. Other antimalarial drugs include artemisinin, 8-aminoquinoline, triazine and biguanide derivatives.

To extensively study the magnitude of potentiation of chloroquine by the chemosensitizers of the present invention, the combined effects of chloroquine and the chemosensitizers were studied as described above by isobologram analysis in an Asian isolate W2 clone. Verapamil was used as a reference drug (control).

Figure 2:
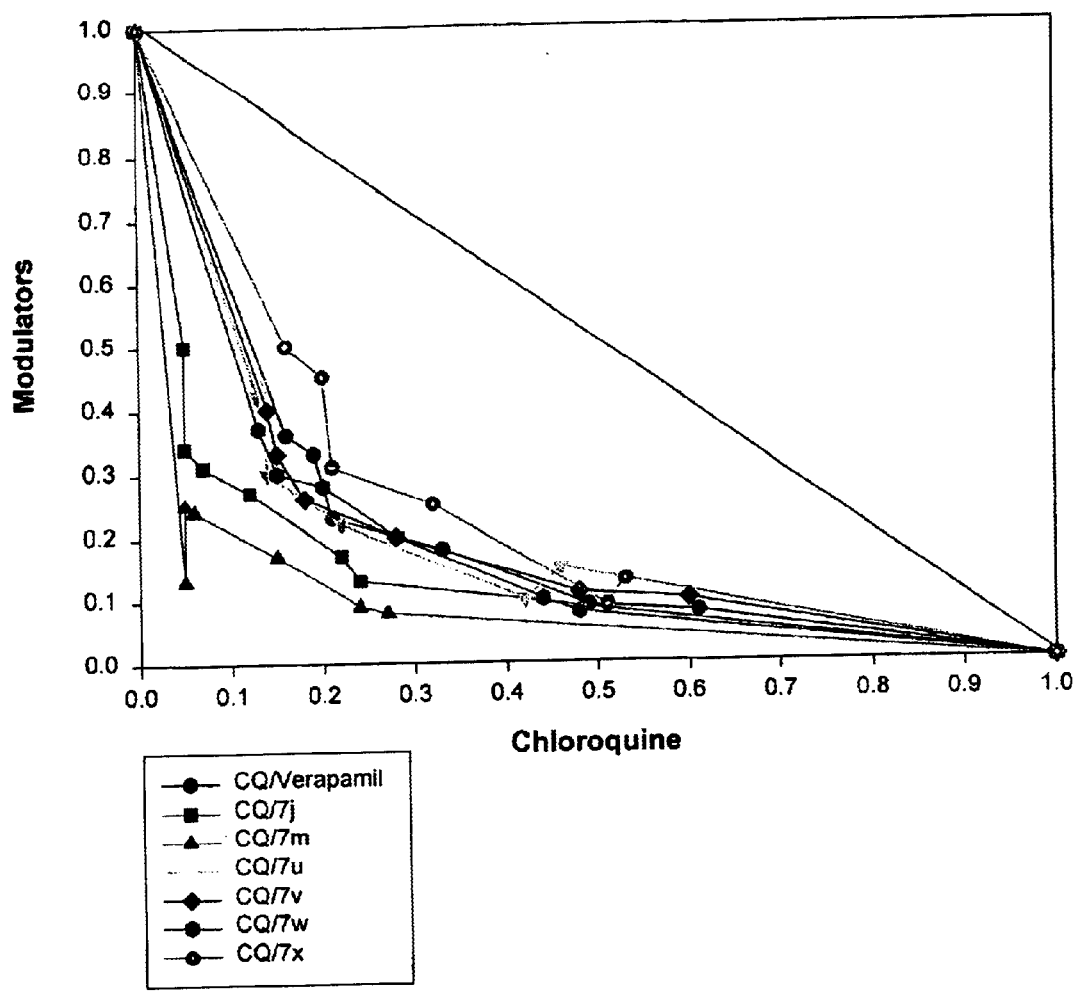
FIG. 2 is an isobologram of the interaction of chloroquine with imipramine derivatives against W2 clone.
Figure 3:
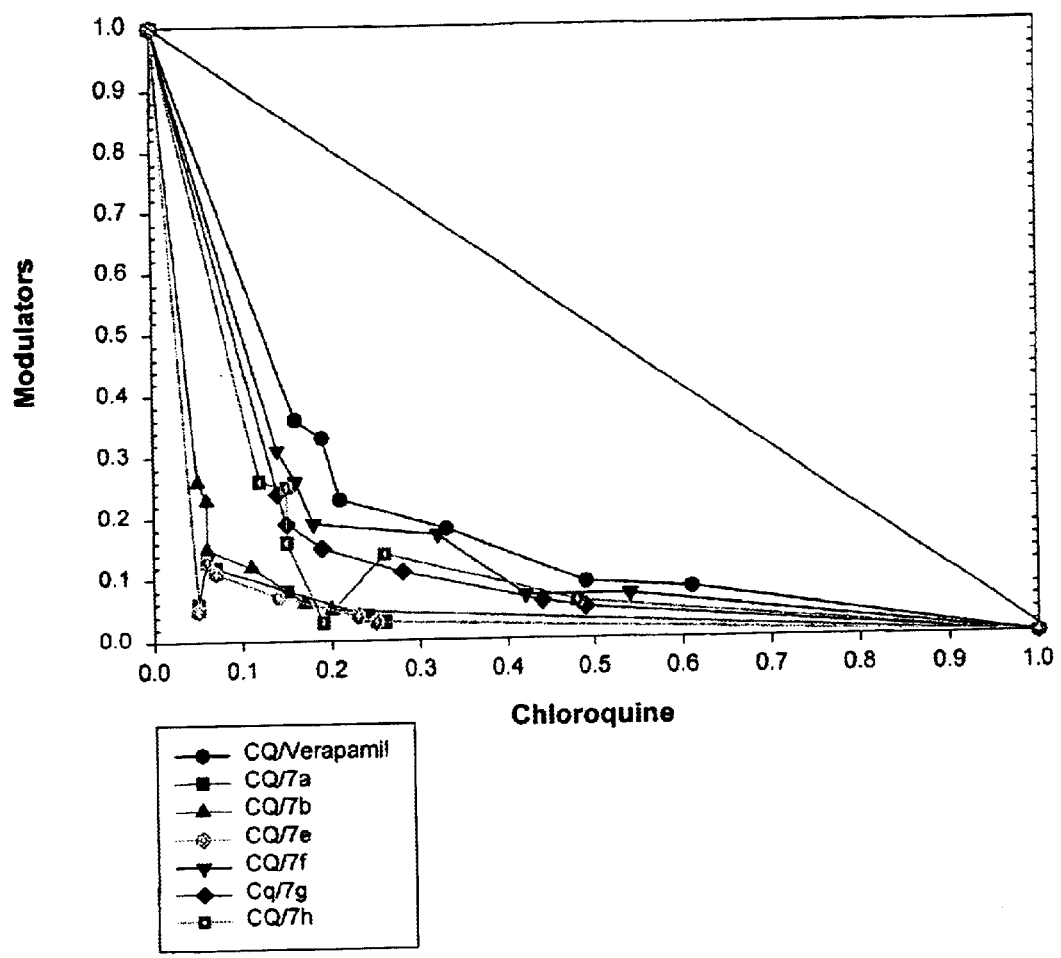
FIG. 3 is an isobologram of the interaction of chloroquine with phenothiazine derivatives against W2 clone.

In the isobologram graphs as shown in FIGS. 1–3, the x-axis is fractional inhibitory concentration (FIC) of chloroquine and the y-axis is FIC of chemosensitizing agent. The FIC is the actual $IC_{50}$ of one drug in the presence of the second drug but is expressed as a fraction of its $IC_{50}$ when used alone. If the isobologram graph is a straight line, it represents an additive effect of the two drugs. If the graph forms a concave curve below the line, it indicates synergy or potentiation of the combination. Below the line means synergy or potentiation and above the line means antagonism. Thus, the more concave the curve, the more effective the modulator. For easy comparison, the FIC index of each test compound is shown in Table 3.

TABLE 3

FIC[1] Indices of New Modulators in Plasmodium falciparum W2 clone[2]

| compound | X | n | Y | $R_1$ | $R_2$ | FIC* |
|---|---|---|---|---|---|---|
| 7a | S | 4 | — | $CH_3$ | $CH_3$ | 0.23 |
| 7b | S | 4 | — | $C_2H_5$ | $C_2H_5$ | 0.23 |
| 7e | S | 4 | pyrrolidinyl | — | — | 0.21 |
| 7f | S | 4 | piperidinyl | — | — | 0.49 |
| 7g | S | 4 | morpholinyl | — | — | 0.39 |
| 7h | S | 4 | 4-methylpiperazinyl | — | — | 0.4 |
| 7i | $C_2H_4$ | 4 | — | $CH_3$ | $CH_3$ | 0.23 |
| 7j | $C_2H_4$ | 4 | — | $C_2H_5$ | $C_2H_5$ | 0.39 |
| 7m | $C_2H_4$ | 4 | pyrrolidinyl | — | — | 0.32 |
| 7n | $C_2H_4$ | 4 | piperidinyl | — | — | 0.45 |
| 7o | $C_2H_4$ | 4 | morpholinyl | — | — | 0.31 |
| 7p | $C_2H_4$ | 4 | 4-methylpiperazinyl | — | — | 0.52 |
| 7q | $C_2H_2$ | 4 | — | $C_2H_5$ | $C_2H_5$ | 0.53 |
| 7r | $C_2H_2$ | 4 | pyrrolidinyl | — | — | 0.33 |
| 7s | N/A | 4 | — | $C_2H_5$ | $C_2H_5$ | 0.48 |
| 7t | N/A | 4 | pyrrolidinyl | — | — | 0.45 |
| 7u | $C_2H_4$ | 5 | — | $C_2H_5$ | $C_2H_5$ | 0.44 |
| 7v | $C_2H_4$ | 5 | pyrrolidinyl | — | — | 0.48 |
| 7w | $C_2H_4$ | 6 | — | $C_2H_5$ | $C_2H_5$ | 0.48 |
| 7x | $C_2H_4$ | 6 | pyrrolidinyl | — | — | 0.57 |
| verapamil | — | — | — | — | — | 0.51 |

[1]FIC = Fractional inhibitory concentration (1:1 combination of drug and chloroquine).
[2]Resistant to chloroquine.

To study the effects of the polycyclic aromatic moiety on the anti-MDR activity, test compounds having four different aromatic rings, phenothiazine, iminodibenzyl, iminostilbene and flexible diphenylamino were prepared and analyzed as described above. The structure-activity relationship is presented in FIG. 1.

Phenothiazine analogs 7b and 7e, which were represented by the most concave curves in FIG. 1, showed the best, greatest or more potent MDR-reversing activity. The FIC indices of compounds 7b and 7e were 0.23 and 0.21, respectively. Compounds containing saturated (7i and 7m) and unsaturated seven-membered central rings (7q and 7r) possessed similar activity with FIC indices in the range of about 0.32 to about 0.53, but were less active than phenothiazine analogs (7b and 7e). Diphenylamino analogs 7s and 7t were not as potent as their tricyclic ring counterparts, and were two-fold less active than phenothiazines 7b and 7e as compared by their FIC indices as shown in Table 3. Generally, all of these compounds displayed better modulating activity than verapamil.

The MDR-reversing activity is also affected by the length of alkyl bridge which connects hydrophobic aromatic ring and terminal amino group. Elongation of the alkyl side chain of the modulators from 3-carbon to 4–6 carbons retained the chemosensitizing activity. However, the potentiation efficacy decreased as the length of alkyl bridge increased from four carbons to six carbons. This trend was clearly demonstrated in FIG. 2.

For example, the curve of compound 7m, which has a four-carbon alkyl linker, was concave more toward the left of the central line as compared to its five-carbon (7v) and six carbon (7x) analogs. This phenomena indicated that 7m was a more potent anti-MDR agent than 7v and 7x (FIC=0.32 vs 0.48 and 0.57, respectively). A similar relationship was observed with compounds 7j, 7u and 7w.

FIG. 3 shows the effect of a series of phenothiazine derivatives in which the size of terminal amino function was varied. Phenothiazine derivatives having non-cyclic amines 7a (dimethylamino), 7b (diethylamino) and five-membered cyclic amine 7e (FIC values=0.23, 0.23 and 0.21, respectively) were more active or potent chemosensitizers than were those having six-membered cyclic amines, 7f, 7g and 7h (FIC values=0.49, 0.39 and 0.4, respectively).

Reid at al. who studied molecular modeling of phenothiazines and their interaction with the target portion—calmodulin have proposed that there are two binding sites at a distance of one-half helical turn. See Reid, R. E., et al. (1983) J. Theor. Biol. 105:63–76, which is herein incorporated by reference. A hydrophobic pocket containing two aromatic phenylalanine residues interact with the tricyclic nucleus, and a hydrophilic region, which composes of three glutamic acid residues, interacts with the positively charged nitrogen atom of the side chain in an electrostatic manner. According the results herein, the optimal length of the alkyl linker is probably dictated by the distance of the two binding sites. Elongation of the alkyl bridge from 4 carbons to 5 or 6 carbons may affect the binding of the ring nucleus and the amino group of the modulators to their corresponding binding sites thereby resulting in less active compounds. In addition, the compromised activity of compounds 7t and 7s (FIG. 1) as MDR modulators suggest that the structure of diphenylamino is too flexible to fit snugly in the hydrophobic binding pocket. Thus, compounds with restricted tricyclic ring systems are better modulators than flexible diphenylamino analogs. Compounds with a bulky substituent at the side chain amino group interacted poorly with acidic residues aligned in the hydrophilic pocket as indicated by the loss of or weak MDR modulating activity in compounds containing N-methyl N-benzylamino or N,N-dibenzylamino groups.

Parasites from different regions responded differently to the compounds of the present invention. The FIC indices in TM91C235 (Thailand), RCS (Brazil) and Peruvian PC49 (South America) are shown in Table 4. The same assay method described above for W-2 was used except that the strains used were isolated from Thailand, Brazil, and Peru, respectively.

TABLE 4

FIC Indices of New Modulators in Parasites from Different Regions

| compd | TM91C235[1] | RCS[2] | Peruvian PC49[3] |
|---|---|---|---|
| verapamil | 0.46 | 0.63 | 0.61 |
| 7a | 0.28 | 0.51 | NT* |
| 7b | 0.29 | 0.41 | 0.41 |
| 7e | 0.25 | 0.51 | 0.5 |
| 7f | 0.52 | 0.68 | 0.83 |
| 7g | 0.32 | 0.37 | 0.81 |
| 7h | 0.48 | 0.49 | 0.98 |

TABLE 4-continued

FIC Indices of New Modulators in Parasites from Different Regions

| compd | TM91C235[1] | RCS[2] | Peruvian PC49[3] |
|---|---|---|---|
| 7i | 0.26 | 0.52 | 0.62 |
| 7j | 0.41 | 0.57 | 0.57 |
| 7m | 0.42 | 0.51 | 0.66 |
| 7n | 0.54 | 0.36 | 0.73 |
| 7o | 0.54 | 0.89 | 0.78 |
| 7p | 0.54 | 0.66 | NT |
| 7q | 0.33 | 0.39 | 0.6 |
| 7r | 0.49 | 0.59 | 0.74 |
| 7s | 0.3 | 0.33 | NT |
| 7t | 0.32 | 0.37 | NT |
| 7u | 0.48 | 0.36 | 0.82 |
| 7v | 0.55 | 0.37 | 0.59 |
| 7w | 0.59 | 0.72 | NT |
| 7x | 0.54 | 0.60 | 0.92 |

[1]Isolate from Southeast Asian.
[2]Isolate form Brazil.
[3]Isolate form South America.
*Not tested.

In general, the compounds of the present invention exhibited better or more potent anti-MDR activity in W-2, TM91C235 and RCS cell lines than in PC49 cell line. As shown in Table 4, a number of compounds displayed significant reversing or modulating activity in W-2, TM91C235 and RCS (FIC<0.4), but exhibited moderate to marginal activity in PC49.

To determine whether the compounds of the present invention provide anti-MDR activity, a mammalian subject, such as an Aotus monkey, may be used. For example, malaria-naive Panamanian owl monkeys (*Aotus lemurinus lemurinus*) may be used as hosts for chloroquine-resistant *P. falciparum*, following previously described procedures and husbandry protocols as described by Kyle, D. E., et al. (1993) *Am J Trop Med Hyg* 48:126–33, and Rossan, R. N., et al. (1985) *Am J Trop Med Hyg* 34:1037–47, which are herein incorporated by reference.

A model subject infected with chloroquine resistant *P. falciparum* may made by injecting an Aotus monkey with a recrudescent isolate from a Vietnam Smith strain, designated Vietnam Smith/RE, which is resistant to chloroquine as evidenced by limited effects on the parasitemia in Aotus monkeys receiving 20 mg/kg/day of chloroquine for seven days. Each subject will be inoculated intravenously with $5 \times 10^6$ trophozoites of the chloroquine resistant Vietnam Smith/RE strain of *P. falciparum*. This inoculum size produces a parasitemia concentration of at least about $5 \times 10^3/mm^3$ by the fifth day post-inoculation, at which time treatment is begun.

Stock solutions of water-soluble drug may be prepared at appropriate concentrations, as determined by one of ordinary skill in the art, and maintained at 4° C. during the course of treatment. A suspension of water-insoluble drugs may be prepared in about 0.3% methylcellulose just prior to use. All drugs may be administered by gastric intubation in a volume of about 7.0 ml, followed by a rinse of about 7.0 ml of water or about 0.3% methylcellulose. Chloroquine alone or in combination with the test compound may be given orally for a given period of time, such as three or seven consecutive days. A 20 mg/kg dose of chloroquine, given once a day for the given period of time, may be used as a negative control in all experiments. Administration of chloroquine in either three daily doses of 20 mg/kg or seven daily doses of about 5 to about 20 mg/kg is effective at treating infections with chloroquine-susceptible parasites in the Aotus monkey; however, these treatment regimens are not effective against the Vietnam Smith or Vietnam Smith/RE strains. See Kyle, D. E., et al. (1993) and Rossan, R. N., et al. (1985).

Giemsa-stained blood smears may be prepared from all subjects and examined daily for a given period of time, such as from the day after inoculation until the parasitemia is cleared from the subject and to at least seven days thereafter. At that time, blood films may be examined twice a week up to about 100 days after treatment. Thick blood films are considered negative if no parasites are seen after examination for at least five minutes. Parasitemia will be enumerated by the Earle-Perez technique as described by Rossan, R. N., et al. (1985), and expressed as the number of parasites/mm$^3$. Ten or less parasites on a thick blood film may be recorded as<10/mm$^3$. Treated subjects may be observed twice a day for signs of drug toxicity, as evidenced by abnormal behavior, anorexia, diarrhea, or vomiting. Necropsies may be performed on all subjects that die.

The classification of treatment results may be determined by the method described by Schmidt, L. H. (1978) *Am J Trop Med Hyg* 27:703–17, which is herein incorporated by reference, or a modified method thereof and the outcome of each infection compared with untreated controls and subjects treated with chloroquine or the test compound alone. The infection will be considered suppressed when the parasitemia persists throughout treatment, but is reduced to 1/50 the level of parasitemia in the control subjects on the same day post-initiation of treatment. An infection will be considered cleared if the parasitemia becomes negative by 12 days after the infection becomes patent and remains negative for seven days; clearance of parasitemia after the infection is patent for 12 days will be attributed to a drug affect. An infection will be considered cured if the parasitemia clears and blood films remain negative for 100 days after the end of treatment. Infections that fail to be cured by the initial treatment will be subsequently treated with higher doses of the test compound in combination with either chloroquine or mefloquine. Re-treatment data will not be considered in the analysis of drug efficacy because of the high rate of self-limiting infections (about 73%) observed in this model. See Kyle et al. (1993). Clear evidence of drug efficacy can be observed through the peak phase of parasitemia, which is up to about 8 to about 11 days from the initiation of patency. Parasitemia in self-limiting infections begins to decrease about 8 to about 14 days after the initiation of patency.

The evaluation of mefloquine resistance modulator drugs require a different *P. falciparum* isolate to be tested in Aotus monkeys as the Vietnam Smith/RE isolate is susceptible to mefloquine. Recently, a new isolate from Thailand, TM93–1088, has been adapted for growth in Aotus monkeys (Rieckmann, unpublished results). This isolate was taken from a patient at Mahidol University that had failed treatment with mefloquine and then recrudesced after treatment with atovaquone plus pyrimethamine REF. TM93–1088 is resistant to chloroquine, mefloquine, atovaquone, pyrimethamine plus sulfadoxine, and quinine in in vitro drug susceptibility tests. See Schmidt, L. H., et al. (1977) *Antimicrob Agents Chemother* 11:826–43, which is herein incorporated by reference.

The present invention is also directed to pharmaceutical compositions comprising a compound having the general Structural Formula A as follows:

Structural Formula A

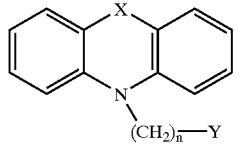

wherein X is a substituted or unsubstituted alkyl or a heteroatom;

n is 4, 5 or 6;

Y is a substituted or unsubstituted alkyl, cycloalkyl, heterocycloalkyl, aryl, heteroaryl, or

wherein $R_1$ and $R_2$ are each independently, H, a heteroatom, substituted or unsubstituted alkyl, cycloalkyl, heterocycloalkyl, aryl, or heteroaryl;

wherein the aromatic ring structures may be each independently further substituted; and a pharmaceutically acceptable excipient In some embodiments of the invention, X is C, S or ethyl.

In some embodiments of the invention, Y is pyrrolidinyl, piperidinyl, morpholinyl, or 4-methylpiperazinyl.

In some embodiments of the invention, $R_1$ or $R_2$ are each independently, methyl, ethyl, or benzyl.

The pharmaceutical compositions according to the invention may, alternatively or in addition to a compound of the Structural Formula A, comprise as an active ingredient a pharmaceutically acceptable salt, prodrug, or active metabolite of such compound or a salt of such a metabolite. Such compounds, salts, prodrugs, and metabolites are sometimes referred to herein collectively as "chemosensitizing agents". Such non-peptide agents are often pharmaceutically advantageous over peptide agents since they provide better biodistribution and tolerance to degradation by physiological enzymes.

A "pharmaceutically acceptable salt" is intended to mean a salt that retains at least the substantial biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrovic acid, oxalic acid, glycolic acid, salicylic acid, a pyranosidyl acid, such as glucuronic acid or galacturonic acid, an alpha-hydrozy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention.

The affinity of the compounds of the invention for a receptor may be enhanced by providing multiple copies of the ligand in close proximity, preferably using a scaffolding provided by a carrier moiety. Such multivalent or multimeric forms of active forms of the compounds of the Structural Formula A are referred to herein as "multimers". Multimers of various dimensions, i.e., bearing varying numbers of copies of an active compound, may be tested to arrive at a multimer of optimum size with respect to receptor binding. Provision of such multivalent forms of active receptor-binding compounds with optimal spacing between the receptor-binding moieties may enhance receptor binding. See, for example, Lee et al. (1984) *Biochem.* 23:4255. The artisan may control the multivalency and spacing by selection of a suitable carrier moiety or linker units. Useful moieties include molecular supports containing a multiplicity of functional groups that can be reacted with functional groups associated with the active compounds of the invention. A variety of carrier moieties may be used to build highly active multimers, including proteins such as BSA (bovine serum albumin) or HAS, peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound.

"A pharmaceutically active metabolite" is intended to mean a pharmacologically active product produced through metabolism in the body of a specified compound or salt thereof.

Prodrugs and active metabolites of a compound may be identified using routine techniques known in the art. See, e.g., Bertolini, G. et al. (1997) *J. Med. Chem.*, 40, 2011–2016; Shan, D. et al., *J. Pharm. Sci.*, 86 (7), 765–767; Bagshawe K. (1995) *Drug Dev. Res.*, 34, 220–230; Bodor, N. (1984) *Advances in Drug Res.*, 13, 224–331; Bundgaard, H., *Design of Prodrugs* (Elsevier Press 1985); and Larsen, I or II. K., Design and Application of Prodrugs, Drug Design and Development. Krogsgaard-Larsen et al., eds., Harwood Academic Publishers (1991).

It is understood that while a compound of Structural Formula A may exhibit the phenomenon of tautomerism, the formula drawings within this specification expressly depict only one of the possible tautomeric forms. It is therefore to be understood that Structural Formula A is intended to represent any tautomeric form of the depicted compound and is not to be limited merely to a specific compound form depicted by the formula drawings.

It is also understood that a compound of Structural Formula A may exist as an "E" or "Z" configurational isomer, or a mixture of E and Z isomers. An E isomer exists when the hydroxy (—OH) substituent of an oxime is on the opposite side of the heterocyclo-portion of a compound; a Z isomer exists when the hydroxy (—OH) substituent is on the same side as the heterocyclo-portion of a compound. It is therefore to be understood that Structural Formula A is intended to represent any configurational form of the depicted compound and is not to be limited merely to a specific compound form depicted by the formula drawings.

Some of the inventive compounds may exist as single stereoisomers, i.e., essentially free of other stereoisomers, racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center, i.e., one asymmetric carbon atom, is one that consists essentially of one of the two possible enantiomers, i.e., is enantiomerically pure, and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess (e.e.) or diastereomeric excess (d.e.)), more preferably at least 95% (90% e.e. or d.e.), even more preferably at least 97.5% (95% e.e. or d.e.), and most preferably at least 99% (98% e.e. or d.e.).

Additionally, the formulas are intended to cover solvated as well as unsolvated forms of the identified structures. For example, Structural Formula A includes compounds of the indicated structure in both hydrated and non-hydrated forms. Other examples of solvates include the structures in combination with isopropanol, ethanol, methanol, DMSO, EtOAc, acetic acid, or ethanolamine.

Compounds and compositions that potently regulate, modulate, attenuate, reverse, or affect a cell or organism's resistance to a given drug or compound are desirable and are one preferred embodiment of the present invention. The present invention is further directed to methods of regulating, modulating, attenuating, reversing, or affecting a cell or organism's resistance to a given drug or compound, by administering the chemosensitizing agent of the present invention.

The chemosensitizing agents in accordance with the present invention are useful for treating MDR in mammals, preferably humans. Preferably, the chemosensitizing agents are useful for treating MDR against antimalarial drugs. Compounds of the Structural Formula A may be used for treating subjects who exhibit MDR or are clinically non-responsive to a given drug therapy. For example, a subject who is not responding to treatment with an antimalarial such as mefloquine or chloroquine, may be administered a chemosensitizing agent of the present invention in conjunction with the antimalarial.

The activity of the inventive compounds as chemosensitizing agents, may be measured by any of the methods available to those skilled in the art, including in vivo and/or in vitro assays such as those set out in the examples below.

In a preferred embodiment, the chemosensitizing agents have a fractional inhibitory concentration of about 0.6 or less, more preferably of about 0.5 or less, more preferably of about 0.4 or less, even more preferably of about 0.3 or less, and further preferably of about 0.2 or less.

The chemosensitizing compounds in accordance with the present invention may be used in combination with a supplementary active compound or as a substitution for treating subjects who exhibit MDR or are clinically non-responsive to a given drug therapy. For example, the chemosensitizing compounds may also be used alone or combination with a supplementary active compound such as an anti-neoplastic agent to treat cancer or an antimalarial to treat malaria. A chemosensitizing compound of the invention may be used alone or in combination with another chemosensitizing agent or the present invention or an antimalarial to treat, prevent or inhibit malaria. Supplementary active compounds include mefloquine, halofantrine, quinine, quinidine, quinacrineartemisinin, artesunic acid, artelinic acid, artemether, arteether, desipramine, haloperidol, imipramine, dipyridamole, penfluridol.

A chemosensitizing compound of the present invention may be administered in a therapeutically effective amount to a mammal such as a human. Therapeutically effective amounts of the chemosensitizing agents of the invention may be used to treat, modulate, attenuate, reverse, or affect a cell's or organism's resistance to a given drug or compound. An "effective amount" is intended to mean that amount of an agent that, when administered to a cell or organism, is sufficient to treat, modulate, attenuate, reverse, or affect the cell's or organism's resistance to a given drug or compound. Thus, e.g., a therapeutically effective amount of a compound of the Structural Formula A, or salt, prodrug, or active metabolite thereof or salt of such metabolite, is a quantity sufficient to treat, modulate, attenuate, reverse, or affect the cell's or organism's resistance to a given drug or compound such that cell or organism responds to the given drug or compound. The amount of a given agent that will correspond to such an amount will vary depending upon factors such as the particular chemosensitizing agent, the given drug or compound, the pharmaceutical formulation and route of administration, the type of drug resistance, and the identity of the subject or host being treated, but can nevertheless be routinely determined by one skilled in the art.

For example, a therapeutically effective amount of a compound of the invention ranges from about 0.1 to about 30 mg/kg body weight, preferably about 0.1 to about 15 mg/kg body weight, and more preferably about 0.1 to about 10 mg/kg body weight. The skilled artisan will appreciate that certain factors may influence the dosage required to effectively treat a subject, including but not limited to the severity of the disease or disorder, previous treatments, the general health and/or age of the subject, and other diseases present.

Moreover, treatment of a subject with a therapeutically effective amount of the chemosensitizing compound can include a single treatment or, preferably, can include a series of treatments.

In a preferred example, a subject is treated with a compound of the invention in the range of between about 0.1 to about 30 mg/kg body weight, at least one time per week for between about one to about three weeks, and preferably between about one to about two weeks. It will also be appreciated that the effective dosage of the compound used for treatment may increase or decrease over the course of a particular treatment. Changes in dosage may result and become apparent by standard diagnostic assays known in the art. In some conditions chronic administration may be required.

The pharmaceutical compositions of the invention may be prepared in a unit-dosage form appropriate for the desired mode of administration. The compositions of the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen active compound.

It will be appreciated that the actual dosages of the agents used in the compositions of this invention will vary according to the particular complex being used, the particular composition formulated, the mode of administration, and the particular site, host, and disease being treated. Optimal dosages for a given set of conditions may be ascertained by those skilled in the art using conventional dosage-determination tests in view of the experimental data for a given chemosensitizing compound. Dosages of prodrugs may be at weight levels that are chemically equivalent to the weight levels of the fully active forms.

The inventive agents may be formulated into pharmaceutical compositions as described below. Pharmaceutical compositions of this invention comprise an effective modulating, regulating, or inhibiting amount of a compound of Structural Formula A and an inert, pharmaceutically acceptable carrier or diluent. In one embodiment of the pharmaceutical compositions, efficacious levels of the inventive agents are provided so as to provide therapeutic benefits involving modulating, attenuating, reversing, or affecting a cell's or organism's resistance to a given drug or compound. By "efficacious levels" is meant levels in which a cell's or organism's resistance to a given drug or compound is, at a minimum, reduced. These compositions are prepared in unit-dosage form appropriate for the mode of administration, e.g., parenteral or oral administration.

The inventive agents may be administered by any of a variety of suitable routes, such as orally, rectally, transdermally, subcutaneously, intravenously, intramuscularly, or intranasally. The agents are preferably formulated into compositions suitable for the desired routes before being administered.

An inventive agent is preferably administered in conventional dosage form prepared by combining a therapeutically effective amount of at least one of the chemosensitizing agents of the invention as an active ingredient with appropriate pharmaceutical carriers or diluents according to conventional procedures. These procedures may involve mixing, granulating and compressing or dissolving the ingredients as appropriate to the desired preparation.

A pharmaceutical composition or preparation according to the invention comprises an effective amount of at least one active ingredient including at least one chemosensitizing agent of the invention and a pharmaceutically acceptable carrier, such as a diluent or excipient for the agent. Other active ingredients include drugs and compounds used for treating, preventing or inhibiting a given disease or disorder. Active ingredients also include the drugs or compounds to which the chemosensitizing agent modulates, attenuates, reverses, or affects a cell's or organism's resistance. For example, a pharmaceutical composition of the present invention may include at least one chemosensitizing agent as disclosed herein and mefloquine as active ingredients to treat, prevent, or inhibit malaria in a subject who may be non-responsive to mefloquine by itself.

When the carrier serves as a diluent, it may be a solid, semi-solid, or liquid material acting as a vehicle, excipient, or medium for the active ingredient. Compositions according to the invention may be made by admixing the active ingredient with a carrier, or diluting it with a carrier, or enclosing or encapsulating it within a carrier, which may be in the form of a capsule, sachet, paper container, or the like. Exemplary ingredients, in addition to one or more cell-cycle control agents and any other active ingredients, include Avicel (microcrystalline cellulose), starch, lactose, calcium sulfate dihydrate, terra alba, sucrose, talc, gelatin, agar, pectin, acacia, magnesium stearate, stearic acid, peanut oil, olive oil, glyceryl monostearate, Tween 80 (polysorbate 80), 1,3-butanediol, cocoa butter, beeswax, polyethylene glycol, propylene glycol, sorbitan monostearate, polysorbate 60, 2-octyldodecanol, benzyl alcohol, glycine, sorbic acid, potassium sorbate, disodium hydrogen phosphate, sodium chloride, and water.

The compositions may be prepared in any of a variety of forms suitable for the desired mode of administration. For example, pharmaceutical compositions may be prepared in the form of tablets, pills, powders, lozenges, sachets, cachets, elixirs, suspensions, emulsions, solutions, syrups, aerosols (as solids or in liquid media), ointments (e.g., containing up to 10% by weight of a cell-cycle control agent), soft-gel and hard-gel capsules, suppositories, sterile injectable solutions, sterile packaged powders, and the like.

Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation can be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an agent can be dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, gylcerin and the like in concentrations ranging from 0–60% of the total volume. In an exemplary embodiment, a compound of Structural Formula A is dissolved in DMSO and diluted with water. The composition may also be in the form of a solution of a salt form of the active ingredient in an appropriate aqueous vehicle such as water or isotonic saline or dextrose solution.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include fillers such as sugars, including lactose, sucrose, mannitol, or sorbitol and cellulose preparations, such as maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For administration to the eye, a compound of the Structural Formula A is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g, containing conventional suppository bases such as cocoa butter or other glycerides.

In addition to the formulations described above, the compounds may also be formulated as a depot preparation.

Such long-acting formulations may be administered by implantation (for example, subcutaneously, intramuscularly, or intraocularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) comprises VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers such as polyvinyl pyrrolidone may replace polyethylene glycol, and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The inventive agents may be prepared using the reaction routes and synthesis schemes as described below, employing the techniques available in the art using starting materials that are readily available.

Other compounds of Structural Formula A may be prepared in manners analogous to the general procedures described above or the detailed procedures described in the examples herein.

The preparation of the preferred compounds of the present invention is described in detail herein, but the artisan will recognize that the chemical reactions described may be readily adapted to prepare a number of other chemosensitizers of the present invention. For example, the synthesis of non-exemplified compounds according to the invention may be successfully performed by modifications apparent to those skilled in the art, e.g., by appropriately protecting interfering groups by changing to other suitable reagents known in the art, or by making routine modifications of reaction conditions. Alternatively, other reactions disclosed herein or known in the art will be recognized as having applicability for preparing other compounds of the invention.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A pharmaceutical composition comprising a compound having the following structural formula:

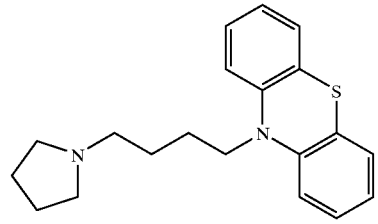

and a pharmaceutically acceptable excipient.

2. The pharmaceutical composition of claim 1 and further comprising an antimalarial.

3. The pharmaceutical composition of claim 2, wherein the antimalarial is selected from the group consisting of 8-aminoquinoline, amodiaquine, arteether, artemether, artemsinin, artesunate, artesunic acid, artelinic acid, atovoquone, azithromycine, biguanide, chloroquine, chloroquine phosphate, chlorproguanil, cycloguanil, dapsone, desbutyl halofantrine, desipramine, doxycycline, dihydrofolate, reductase inhibitors, dipyridamole, halofantrine, haloperidol, hydroxychloroquine sulfate, imipramine, mefloquine, penfluridol, phospholipid inhibitors, primaquine, proguanil, pyrimethamine, pyronaridine, quinine, quinidine, quinacrineartemisinin, sulfonamides, sulfones, sulfadoxine, sulfalene, tafenoquine, tetracycline, tetrandine, triazine, and derivatives thereof.

4. A method of treating malaria in a subject which comprises administering to the subject a therapeutically effective amount of the pharmaceutical composition of claim 2.

5. A method of treating malaria in a subject which comprises administering to the subject a therapeutically effective amount of the pharmaceutical composition of claim 3.

6. A method of treating malaria in a subject which comprises administering to the subject a therapeutically effective amount of a compound having the following structural formula:

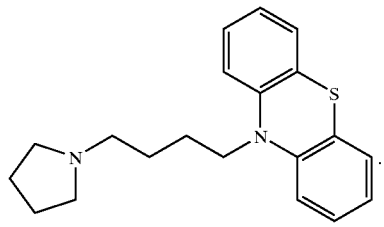

7. The method of claim 6 and further comprising administering an antimalarial.

8. The method of claim 7, wherein the antimalarial is selected from the group consisting of 8-aminoquinoline, amodiaquine, arteether, artemether, artemsinin, artesunate, artesunic acid, artelinic acid, atovoquone, azithromycine, biguanide, chloroquine, chloroquine phosphate, chlorproguanil, cycloguanil, dapsone, desbutyl halofantrine, desipramine, doxycycline, dihydrofolate reductase inhibitors, dipyridamole, halofantrine, haloperidol, hydroxychloroquine sulfate, imipramine, mefloquine, penfluridol, phospholipid inhibitors, primaquine, proguanil, pyrimethamine, pyronaridine, quinine, quinidine, quinacrineartemisinin, sulfonamides, sulfones, sulfadoxine, sulfalene, tafenoquine, tetracycline, tetrandine, triazine, and derivatives thereof.

\* \* \* \* \*